(12) United States Patent
Fischer et al.

(10) Patent No.: US 10,370,437 B2
(45) Date of Patent: Aug. 6, 2019

(54) ANTIBODIES THAT MODULATE IMMUNITY TO DRUG RESISTANT AND LATENT MTB INFECTIONS

(71) Applicant: Longhorn Vaccines and Diagnostics, LLC, Bethesda, MD (US)

(72) Inventors: Gerald W. Fischer, Bethesda, MD (US); Luke T. Daum, San Antonio, TX (US); Richard F. Schuman, Silver Spring, MD (US); Clara J. Sei, Germantown, MD (US)

(73) Assignee: Longhorn Vaccines and Diagnostics, LLC, Bethesda, MD (US)

( * ) Notice: Subject to any disclaimer, the term of this patent is extended or adjusted under 35 U.S.C. 154(b) by 0 days.

(21) Appl. No.: 15/850,208

(22) Filed: Dec. 21, 2017

(65) Prior Publication Data

US 2018/0127488 A1    May 10, 2018

Related U.S. Application Data

(63) Continuation-in-part of application No. 15/275,813, filed on Sep. 26, 2016, which is a continuation-in-part of application No. 14/473,322, filed on Aug. 29, 2014, now Pat. No. 9,821,047.

(60) Provisional application No. 61/872,391, filed on Aug. 30, 2013, provisional application No. 62/232,114, filed on Sep. 24, 2015.

(51) Int. Cl.
| | |
|---|---|
| A61K 39/02 | (2006.01) |
| C07K 16/12 | (2006.01) |
| A61K 45/06 | (2006.01) |
| A61K 39/40 | (2006.01) |
| A61K 39/04 | (2006.01) |
| A61P 31/06 | (2006.01) |
| A61K 39/00 | (2006.01) |

(52) U.S. Cl.
CPC .......... *C07K 16/1289* (2013.01); *A61K 39/04* (2013.01); *A61K 39/40* (2013.01); *A61K 45/06* (2013.01); *A61P 31/06* (2018.01); *A61K 2039/521* (2013.01); *A61K 2039/522* (2013.01); *A61K 2039/545* (2013.01); *A61K 2039/575* (2013.01); *A61K 2039/6037* (2013.01); *C07K 2317/21* (2013.01); *C07K 2317/24* (2013.01); *C07K 2317/52* (2013.01); *C07K 2317/55* (2013.01); *C07K 2317/734* (2013.01)

(58) Field of Classification Search
None
See application file for complete search history.

(56) References Cited

U.S. PATENT DOCUMENTS

| | | | |
|---|---|---|---|
| 7,122,577 | B1 | 10/2006 | Verschoor |
| 9,821,047 | B2 | 11/2017 | Fischer |
| 2001/0007660 | A1 | 7/2001 | Glatman-Freedman |
| 2011/0027349 | A1 | 2/2011 | Sable |
| 2013/0195909 | A1 | 8/2013 | Fischer et al. |
| 2015/0064198 | A1 | 3/2015 | Fischer et al. |
| 2017/0008954 | A1 | 1/2017 | Fischer et al. |

FOREIGN PATENT DOCUMENTS

| | | |
|---|---|---|
| AU | 2014/312135 | 12/2017 |
| WO | WO 2000/021983 | 4/2000 |
| WO | WO 2012/035558 | 3/2012 |
| WO | WO 2012035558 | 3/2012 |
| WO | WO 2012076868 | 6/2012 |
| WO | WO 2015/031787 | 3/2015 |

OTHER PUBLICATIONS

Examination Report for AU Application No. 2017272266 dated Sep. 13, 2018.
EP Search Report for App. No. EP 14839667, dated Mar. 10, 2017.
Bertholet S et al: "A Defined Tuberculosis Vaccine Candidate Boosts BCG and Protects Against Mulidrug Resistant Mycobacterium tuberculosis", Science Translational Medicine, vol. 2, No. 53, Oct. 13, 2010, pp. 64-71.
Eduardo Martins De Sousa et al. "Immunogenicity of a Fusion Protein Containing Immunodominant Epitopes of Ag85C, MPT51, and HspX from Mycobacterium tuberculosis in Mice and Active TB Infection", Plos One, vol. 7, No. 10, Oct. 25, 2012, p. e47781.
Niu Hongxia et al: "Construction and Evaluation of a Multistage Mycobacterium Tuberculosis Subunit Vaccine Candidate Mtb10.4-HspX", Vaccine, Elsevier, Amsterdam, NL, vol. 20, No. 51, Oct. 15, 2011, pp. 9451-9458.
A Glatman-Freedman et al: "Monoclonal Antibodies to Surface Antigens of Mycobacterium Tuberculosis and Their Use in a Modified Enzyme-Linked Immunosorbent Spot Assay for Detection of Mycobacteria", Journal of Clinical Microbiology, Nov. 1, 1996, pp. 2795-2802.

(Continued)

*Primary Examiner* — Jennifer E Graser
(74) *Attorney, Agent, or Firm* — Remenick PLLC

(57) ABSTRACT

The invention is directed to compositions and methods for stimulating, enhancing or modulating the immune system of a patient before or after infection by a pathogen, and in particular multidrug resistant (MDR) MTB and extremely drug resistant (XDR) MTB. Compositions of the invention contain non-naturally occurring antigens that generate an effective cellular and/or humoral immune response to MTB and/or antibodies that are specifically reactive to MTB antigens. The greater activity of the immune system generated by a vaccine of the invention increases generation of memory T cells that provide for a greater and/or extended response to an MTB infection. Responses involve an increased generation of antibodies that enhance immunity against MTB infection and promote an enhanced phagocytic response. Monoclonal antibodies produced by the non-naturally occurring antigens enhance phagocytosis and killing of mycobacteria by phagocytic cells, enhance clearance of MTB from the blood and modulate immunity and cytokine responses.

18 Claims, 13 Drawing Sheets

Figure 1:
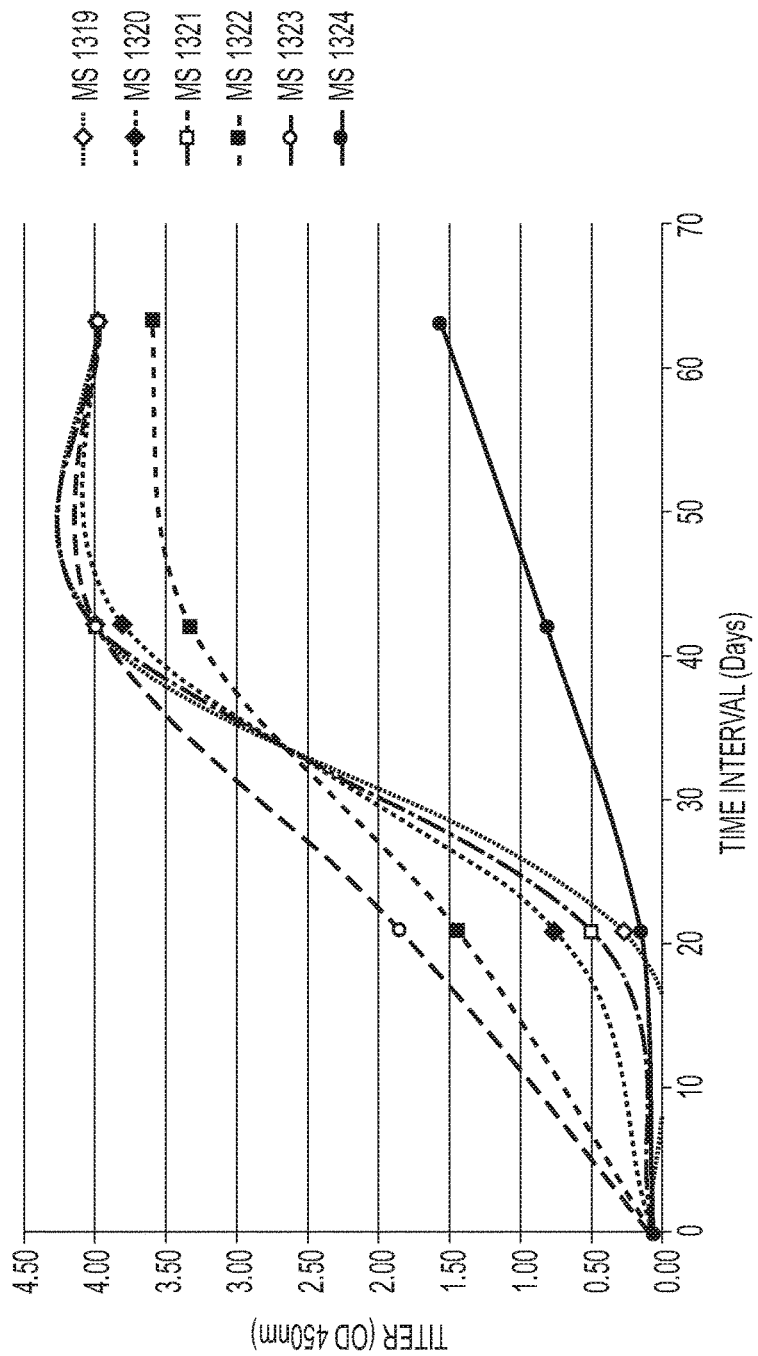

Specification includes a Sequence Listing.

(56) References Cited

OTHER PUBLICATIONS

Dietrich Jes et al: "Exchanging ESAT6 with TB10.4 in an Ag85B fusion molecule-based tuberculosis subunit vaccine: Efficient protection and ESAT6-based sensitive monitoring of vaccine efficacy", The Journal of Immunology, The American Association of Immunologists, vol. 174, No. 10, May 1, 2005, pp. 6332-6339.
B. Hamasur et al.: "A Mycobacterial Lipoarabinomannan Specific Monoclonal Antibody and its F(ab')2 Fragment Prolong Survival of Mice Infected with Mycobacterium Tuberculosis", Clinical & Experimental Immunology, vol. 138, No. 1, Oct. 1, 2004, pp. 30-38.
Anke K. Trilling et al: "A Broad Set of Different Llama Antibodies Specific for a 16 kDa Heat Shock Protein of Mycobacterium Tuberculosis" Plos One, vol. 6, No. 10, Oct. 26, 2011, p. e26754.
S. Manivannan et al. "Role of Complement Activation and Antibody in the Interaction Between Mycobacterium Tuberculosis and Human Macrophages", Indian Journal of Experimental Biology, Aug. 1, 2012, pp. 542-550.
AU Examination Report for 2014/312135 dated Sep. 6, 2016.
AU Examination Report for 2014/312135 dated Aug. 14, 2017.
Trilling et al. (PLoS One) (2011) (6)10 e26754 pp. 1-10.
Zhou et al. Hybridoma 2011 30(5) pp. 427-432.
Greenspan et al. Nature BioTechnology 7:936-937 1999.
MacCallum et al., J. Mol. Biol. (1996) 262:732-745.
Rudikoff et al., Proc. Natl. Acad. Sci. 1982 vol. 79 p. 1979.
Pascalis et al. The Journal of Immunology (2002) 169:3076-3084.
Casset et al. (2003) BBRC 307, 198-205.
Wu et al. J. Mol. Biol. (1999) 294, 151-162.
Hamasur, B. et al., 'A new rapid and simple method for large-scale purification of mycobacterial lipoarabinomannan', FEMS Immunology and Medical Microbiology. 1999, vol. 24, pp. 11-17.
Examination Report for AU Application No. 2017272265 dated Sep. 13, 2018.
Examination Report for CN Application No. 201480059768.4 dated Aug. 10, 2018 (translation).
Examination Report for CN Application No. 201480059768.4 dated Aug. 10, 2018.
Hongxia Niu et al., "Construction and evaluation of a multistage mycobacterium tuberculosis subunit vaccine candidate Mtb10.4-HspX", Vaccine, vol. 29, p. 9451-9458, Oct. 21, 2011.
Examination Report for IN Application No. 201617005516 dated Mar. 5, 2019.
S. Bertholet et al., "A Defined Tuberculosis Vaccine Candidate Boosts BCG and Protects Against Multidrug Resistant Mycobacterium tuberculosis" Sci. Transl. Med. vol. 2(53):53, Oct. 13, 2010.
Eduardo Martins De Sousa et al., "Immunogenicity of a Fusion Protein Containing immunodominant Epitopes of Ag85C, MPT51, and HspX from Mycobacterium tuberculosis in Mice and Active TB Infection" Plus One 7(10):e47781, Oct. 25, 2012.
E.T. Glatman-Freedman, "Monoclonal antibodies to surface antigens of Mycobacterium tuberculosis and their use in a modified enzyme linked immunosorbent spot assay for detection of mycobacteria" Journal of Clinical Microbiology, vol. 34(11):2795-2802, Nov. 1, 1996.
J. Dietrich et al., "Exchanging ESAT6 with TB10.4 in an Ag85B fusion molecule based tuberculosis subunit vaccine: Efficient protection and ESAT6-based sensitive monitoring of vaccine efficacy" Journal of Immunology, vol. 174(10):6332, May 15, 2005.
Anke K. Trilling et al., "A Broad Set of Different Llama Antibodies Specific for a 16 kDa Heat Shock Protein of Mycobacterium tuberculosis" Plus One, 6(10):e26754, Oct. 26, 2011.

OPSONOPHAGOCYTIC MYCOBACTERIAL KILLING ASSAY:
EFFECT OF MAB WITH HL60 CELLS AND C1q

| | % C1q | M. SMEGMATUS KILLED<br>GG9 II F2 (10-25 ug/ml) |
|---|---|---|
| 4/12 | 0 | 58% |
| 5/22 | 0 | 55% |
| 5/22 | 0 | 50% |
| 5/29 | 0 | 54% |
| AVERAGE | 0* | 54% |

*≥ 50% KILLING FOR OPBA, FLECK ET AL., CLIN AND DIAG LAB IMMUN, 2005

FIG. 8

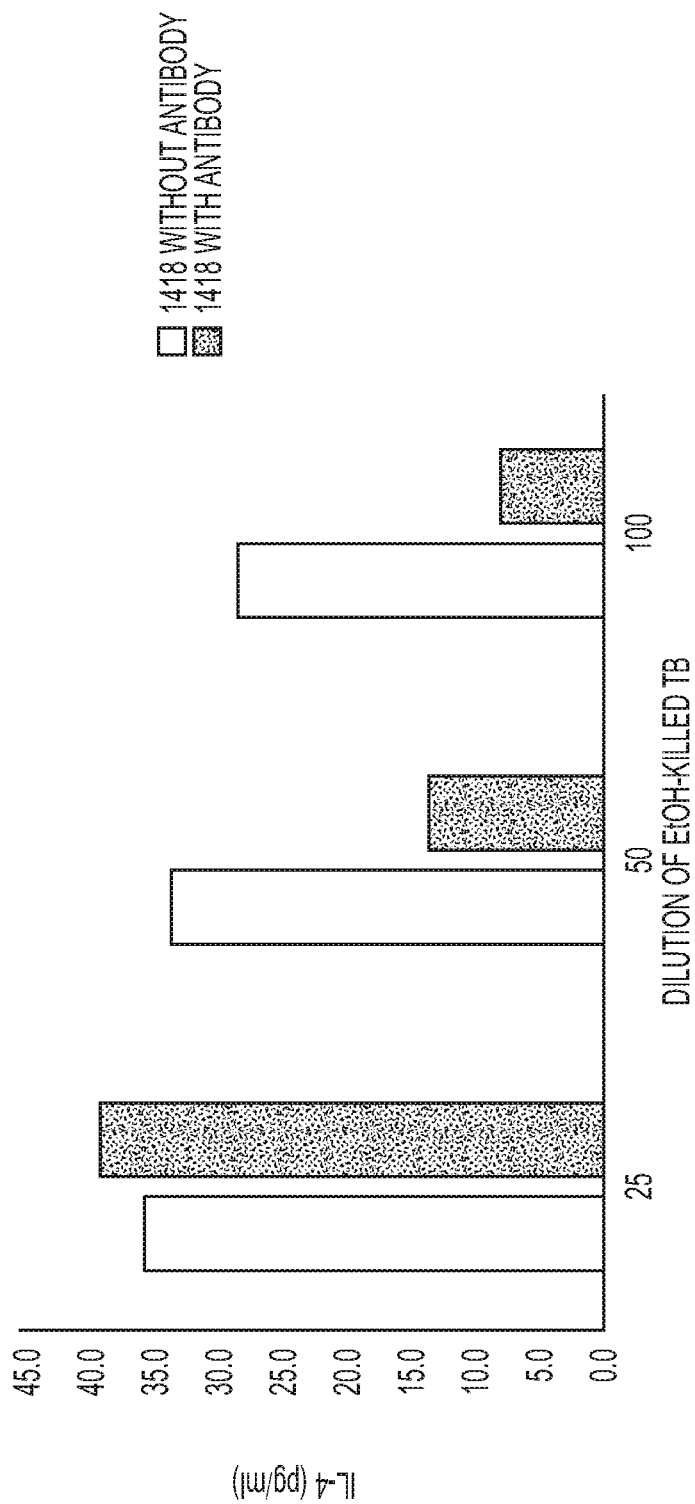

```
                            SEQUENCE LISTING

<160> NUMBER OF SEQ ID NOS: 10

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Glu Phe Ala Tyr Gly Ser Phe Val Arg Thr Val Ser Leu Pro Val
1               5                   10                  15

Gly Ala Asp Glu
            20

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Asn Leu Phe Ile Ala Pro
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

His Tyr Glu Glu Cys Ser Cys Tyr
1               5

<210> SEQ ID NO 4
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 4

Trp Gly Val Ile His His Pro
1               5

<210> SEQ ID NO 5
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Asn Leu Phe Ile Ala Pro Trp Gly Val Ile His His Pro His Tyr
1               5                   10                  15

Glu Glu Cys Ser Cys Tyr
            20

<210> SEQ ID NO 6
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Trp Gly Val Ile His His Pro Gly Asn Leu Phe Ile Ala Pro His Tyr
1               5                   10                  15

Glu Glu Cys Ser Cys Tyr
            20

<210> SEQ ID NO 7
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ser Glu Phe Ala Tyr Gly Ser Phe Val Arg Thr Val Ser Leu Pro Val
1               5                   10                  15

Gly Ala Asp Glu Gly Asn Leu Phe Ile Ala Pro Trp Gly Val Ile His
                20                  25                  30

His Pro His Tyr Glu Glu Cys Ser Cys Tyr
            35                  40

<210> SEQ ID NO 8
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gly Asn Leu Phe Ile Ala Pro Trp Gly Val Ile His His Pro His Tyr
1               5                   10                  15

Glu Glu Cys Ser Cys Tyr Ser Glu Phe Ala Tyr Gly Ser Phe Val Arg
            20                  25                  30
```

```
Thr Val Ser Leu Pro Val Gly Ala Asp Glu
        35                  40

<210> SEQ ID NO 9
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

His Tyr Glu Glu Cys Ser Cys Tyr Ser Glu Phe Ala Tyr Gly Ser Phe
1               5                   10                  15

Val Arg Thr Val Ser Leu Pro Val Gly Ala Asp Glu
            20                  25

<210> SEQ ID NO 10
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Glu Phe Ala Tyr Gly Ser Phe Val Arg Thr Val Ser Leu Pro Val
1               5                   10                  15

Gly Ala Asp Glu His Tyr Glu Glu Cys Ser Cys Tyr
            20                  25
```

ANTIBODIES THAT MODULATE IMMUNITY TO DRUG RESISTANT AND LATENT MTB INFECTIONS

REFERENCE TO RELATED APPLICATIONS

This application is a continuation-in-part of U.S. application Ser. No. 15/275,813 entitled "Monoclonal Antibodies that Modulate Immunity to MTB and Enhance Immune Clearance" filed Jul. 26, 2016, which is a continuation-in-part of U.S. application Ser. No. 14/473,322 entitled "Enhancing Immunity to Tuberculosis" filed Aug. 29, 2014 which issued as U.S. Pat. No. 9,821,047 Nov. 11, 2017, which claims priority to U.S. Provisional Application No. 61/872,391 filed Aug. 30, 2013, and claims priority to U.S. Provisional Application No. 62/232,117 filed Sep. 24, 2015, the entirety of each of which is specifically incorporated by reference.

SEQUENCE LISTING

The instant application contains a Sequence Listing which has been submitted electronically in ASCII format and is hereby incorporated by reference in its entirety. Said ASCII copy, created on Aug. 28, 2014, is named 3022.035.PCT_SL.txt and is 3,775 bytes in size.

BACKGROUND

1. Field of the Invention

The present invention is directed to compositions and methods for treating a disease or disorder and/or enhancing the immune system of a patient and, in particular, vaccines of non-naturally occurring substances and vaccination methods for treating and/or enhancing the immune system against infection by multidrug resistant (MDR) MTB, extremely drug resistant (XDR), and latent *Mycobacterium tuberculosis*.

2. Description of the Background

*Mycobacterium tuberculosis* (MTB) is a pathogenic bacterial species in the family Mycobacteriaceae and the causative agent of most cases of tuberculosis (TB). Another species of this genus is *M. leprae*, the causative agent of leprosy. MTB was first discovered in 1882 by Robert Koch, *M. tuberculosis* has an unusual, complex, lipid rich, cell wall which makes the cells impervious to Gram staining. Acid-fast detection techniques are used to make the diagnosis instead. The physiology of *M. tuberculosis* is highly aerobic and requires significant levels of oxygen to remain viable. Primarily a pathogen of the mammalian respiratory system, MTB is generally inhaled and, in five to ten percent of individuals, will progress to an acute pulmonary infection. The remaining individuals will either clear the infection completely or the infection may become latent. It is not clear how the immune system controls MTB, but cell mediated immunity is believed to play a critical role (Svenson et al., Human Vaccines, 6-4:309-17, 2010). Common diagnostic methods for TB are the tuberculin skin test, acid-fast stain and chest radiographs.

Well over ninety percent of individuals infected with MTB remain outwardly healthy with no demonstrable symptoms. These individuals are classified as latently infected and are a reservoir from which active MTB cases continue to develop ("reactivation tuberculosis"). Latent infection is generally defined as the absence of clinical symptoms of TB in addition to a delayed hypersensitivity reaction to the purified protein derivative of MTB used in tuberculin skin test or a T-cell response to MTB-specific antigens. The absence of an understanding of latency and thereby reliable control measures for treatment, makes latent tuberculosis infections a serious problem.

*M. tuberculosis* requires oxygen to proliferate and does not retain typical bacteriological stains due to high lipid content of its cell wall. While mycobacteria do not fit the Gram-positive category from an empirical standpoint (i.e., they do not retain the crystal violet stain), they are classified as acid-fast Gram-positive bacteria due to their lack of an outer cell membrane.

*M. tuberculosis* has over one hundred strain variations and divides every 15-20 hours, which is extremely slow compared to other types of bacteria that have division times measured in minutes (*Escherichia coli* can divide roughly every 20 minutes). The microorganism is a small bacillus that can withstand weak disinfectants and survive in a dry state for weeks. The cell wall of MTB contains multiple components such as peptidoglycan, mycolic acid and the glycolipid lipoarabinomannan. The role of these moieties in pathogenesis and immunity remain controversial. (Svenson et al., Human Vaccines, 6-4:309-17, 2010).

MTB infection is spread by airborne droplet nuclei, which contain the pathogen expelled from the lungs and airways of those with active TB. The infectious droplet nuclei are inhaled and lodge in the alveoli and in the alveolar sac where *M. tuberculosis* is taken up by alveolar macrophages. These macrophages invade the subtending epithelial layer, which leads to a local inflammatory response initiating formation of the granuloma, the hallmark of tuberculosis disease. That results in recruitment of mononuclear cells from neighboring blood vessels, thus providing fresh host cells for the expanding bacterial population. However, these macrophages are unable to digest the bacteria because the cell wall of the bacteria prevents the fusion of the phagosome with a lysosome. Specifically, *M. tuberculosis* blocks the bridging molecule, early endosomal autoantigen 1 (EEA1); however, this blockade does not prevent fusion of vesicles filled with nutrients. As a consequence, bacteria multiply unchecked within the macrophage. The bacteria also carry the UreC gene, which prevents acidification of the phagosome, and also evade macrophage-killing by neutralizing reactive nitrogen intermediates.

With the arrival of lymphocytes, the granuloma acquires a more organized, stratified structure. Development of an immune response takes about 4-6 weeks after the primary infection is indicated by a positive DTH (delayed type hypersensitivity) reaction to Tuberculin. The balance between host immunity (protective and pathologic) and bacillary multiplication determines the outcome of infection. An encounter with MTB is classically regarded to give rise to three possible outcomes. The first possible outcome, which occurs in a minority of the population, is the rapid development of active TB and associated clinical symptoms. The second possible outcome, which occurs in the majority of infected individuals, do not include disease symptoms. These individuals develop an effective acquired immune response and are considered to have a "latent infection." A portion of latently infected individuals over time will reactivate and develop active TB. Roughly ten percent of these infected individuals (mainly infants or children) will develop progressive clinical disease referred to as primary active TB. Primary TB usually occurs within 1-2 years after the initial infection. This results from local bacillary multiplication and spread in the lung and/or blood. Spread through the blood can seed bacilli in various tissues and organs. Post-primary, or secondary, TB can occur many years after infection owing to loss of immune control and the reactivation of bacilli. The immune response of the patient results in a pathological lesion that is characterized by localized, often extensive tissue damage, and cavitations. The characteristic features of active post-primary TB can include extensive lung destruction with cavitation, positive sputum smear (most often), and upper lobe involvement, however these are not exclusive. Patients with cavitary lesions (i.e., granulomas that break through to an airway) are the main transmitters of infection. In latent TB, the host immune response is capable of controlling the infection but falls short of eradicating the pathogen. Latent TB is defined on solely on the evidence of sensitization by mycobacterial proteins that is a positive result in either the Tuberculin skin test (TST) reaction to purified protein derivative of MTB or an in vitro interferon-gamma (IFN-γ) release assay to MTB-specific antigens, in the absence of clinical symptoms or isolated bacteria from the patient.

The BCG vaccine (Bacille de Calmette et Guérin) against tuberculosis is prepared from a strain of the attenuated, but live bovine tuberculosis bacillus, *Mycobacterium bovis*. This strain lost its virulence to humans through in vitro subculturing in Middlebrook 7H9 media. As the bacteria adjust to subculturing conditions, including the chosen media, the organism adapts and in doing so, loses its natural growth characteristics for human blood. Consequently, the bacteria can no longer induce disease when introduced into a human host. However, the attenuated and virulent bacteria retain sufficient similarity to provide immunity against infection of human tuberculosis. The effectiveness of the BCG vaccine has been highly varied, with an efficacy of from zero to eighty percent in preventing tuberculosis for duration of fifteen years, although protection seems to vary greatly according to geography and the lab in which the vaccine strain was grown. This variation, which appears to depend on geography, generates a great deal of controversy over use of the BCG vaccine yet has been observed in many different clinical trials. For example, trials conducted in the United Kingdom have consistently shown a protective effect of sixty to eighty percent, but those conducted in other areas have shown no or almost no protective effect. For whatever reason, these trials all show that efficacy decreases in those clinical trials conducted close to the equator. In addition, although widely used because of its protective effects against disseminated TB and TB meningitis in children, the BCG vaccine is largely ineffective against adult pulmonary TB, the single most contagious form of TB.

A 1994 systematic review found that the BCG reduces the risk of getting TB by about fifty percent. There are differences in effectiveness, depending on region due to factors such as genetic differences in the populations, changes in environment, exposure to other bacterial infections, and conditions in the lab where the vaccine is grown, including genetic differences between the strains being cultured and the choice of growth medium.

The duration of protection of BCG is not clearly known or understood. In studies showing a protective effect, the data are inconsistent. The MRC study showed protection waned to 59% after 15 years and to zero after 20 years; however, a study looking at Native Americans immunized in the 1930s found evidence of protection even 60 years after immunization, with only a slight waning in efficacy. Rigorous analysis of the results demonstrates that BCG has poor protection against adult pulmonary disease, but does provide good protection against disseminated disease and TB meningitis in children. Therefore, there is a need for new vaccines and vaccine antigens that can provide solid and long-term immunity to MTB.

The role of antibodies in the development of immunity to MTB is controversial. Current data suggests that T cells, specifically $CD4^+$ and $CD8^+$ T cells, are critical for maximizing macrophage activity against MTB and promoting optimal control of infection (Slight et al, JCI 123(2):712, February 2013). However, these same authors demonstrated that B cell deficient mice are not more susceptible to MTB infection than B cell intact mice suggesting that humoral immunity is not critical. Phagocytosis of MTB can occur via surface opsonins, such as C3, or nonopsonized MTB surface mannose moieties. Fc gamma receptors, important for IgG facilitated phagocytosis, do not seem to play an important role in MTB immunity (Crevel et al., Clin Micro Rev. 15(2), April, 2002; Armstrong et al., J Exp Med. 1975 Jul. 1; 142(1):1-16). IgA has been considered for prevention and treatment of TB, since it is a mucosal antibody. A human IgA monoclonal antibody to the MTB heat shock protein HSPX (HSPX) given intra-nasally provided protection in a mouse model (Balu et al, J of Immun. 186:3113, 2011). Mice treated with IgA had less prominent MTB pneumonic infiltrates than untreated mice. While antibody prevention and therapy may be hopeful, the effective MTB antigen targets and the effective antibody class and subclasses have not been established (Acosta et al, Intech, 2013).

Cell wall components of MTB have been delineated and analyzed for many years. Lipoarabinomannan (LAM) has been shown to be a virulence factor and a monoclonal antibody to LAM has enhanced protection to MTB in mice (Teitelbaum, et al., Proc. Natl. Acad. Sci. 95:15688-15693, 1998, Svenson et al., Human Vaccines, 6-4:309-17, 2010). The mechanism whereby the MAB enhanced protection was not determined and the MAB did not decrease bacillary burden. It was postulated that the MAB possibly blocked the effects of LAM induced cytokines. The role of mycolic acid for vaccines and immune therapy is unknown. It has been used for diagnostic purposes, but has not been shown to have utility for vaccine or other immune therapy approaches. While MTB infected individuals may develop antibodies to mycolic acid, there is no evidence that antibodies in general, or specifically mycolic acid antibodies, play a role in immunity to MTB.

Antibiotic resistance is becoming more and more of a problem for treating MTB infections. Beginning with the first antibiotic treatment for TB in 1943, some strains of the TB bacteria developed resistance to the standard drugs through genetic changes. The BCG vaccine against TB does not provide protection from acquiring TB to a significant degree. In fact, resistance accelerates if incorrect or inadequate treatments are used, leading to the development and spread of multidrug-resistant TB (MDR-TB). Incorrect or inadequate treatment may be due to use of the wrong medications, use of only one medication (standard treatment is at least two drugs), not taking medication consistently or for the full treatment period (treatment is required for several months). Treatment of MDR-TB requires second-line drugs (e.g., fluoroquinolones, aminoglycosides, and others), which in general are less effective, more toxic and much more expensive than first-line drugs. If these second-line drugs are prescribed or taken incorrectly, further resistance can develop leading to extreme-drug resistant TB (XDR-TB). Resistant strains of TB are already present in the population, so MDR-TB and XDR-TB are directly transmitted from an infected person to an uninfected person.

Thus, a previously untreated person can develop a new case of MDR-TB or XDR-TB absent prior infection and/or treatments. This is known as primary MDR-TB or XR-TB and is responsible for up to 75% of new TB cases. Acquired MDR-TB and XR-TB develops when a person with a non-resistant strain of TB is treated inadequately, resulting in the development of antibiotic resistance in the TB bacteria infecting them. These people can in turn infect other people with MDR-TB.

Drug-resistant TB caused an estimated 480,000 new TB cases and 250,000 deaths in 2015, and accounts for about 3.3% of all new TB cases worldwide. These resistant forms of TB bacteria, either MDR-TB or rifampin-resistant TB, cause 3.9% of new TB cases and 21% of previously treated TB cases. Globally, most drug-resistant TB cases occur in South America, Southern Africa, India, China, and areas of the former Soviet Union.

Treatment of MDR-TB requires treatment with second-line drugs, usually four or more anti-TB drugs for a minimum of 6 months, and possibly extending for 18-24 months if rifampin resistance has been identified in the specific strain of TB with which the patient has been infected. Under ideal program conditions, MDR-TB cure rates can approach 70%. XR-TB infection requires even more-robust and prolonged treatment regiments.

Thus there is a strong need to provide or improve products and approaches to prevent and treat drug-resistant MTB.

SUMMARY OF THE INVENTION

The present invention overcomes the problems and disadvantages associated with current strategies and designs and provide new tools and methods for enhancing the immune system.

One embodiment of the invention is directed to an immunological composition comprising antibodies and preferably monoclonal antibodies for the treatment or prevention of infection of drug-resistant *Mycobacterium tuberculosis* (MTB) in a mammal. Preferably, antibodies of the invention induce opsinization and/or killing of microorganisms and in particular MTB. Antibodies of the invention are specifically reactive and bind one or more MTB epitopes that may be chemically or physically altered. Antibodies may be produced through recombinant techniques, such as humanization of murine antibodies preferably including a pharmaceutically acceptable carrier. Preferably the antibody-reactive antigen comprises an MTB surface secreted or intracellular antigen. Preferably the antigen comprises one or more of an MTB surface antigen, a synthetic MTB peptide, a synthetic composite peptide, or a combination thereof. Preferably the antibodies are specifically reactive against an MTB antigen wherein the MTB has been alcohol-killed, such as with ethanol, heat-killed, or gluteraldehyde-killed. The alcohol for example denatures the proteins and disassociates the lipid structures in the cell wall producing new and altered (non-natural) molecules. Preferably the pharmaceutically acceptable carrier comprises water, oil, fatty acid, carbohydrate, lipid, cellulose, or a combination thereof. Preferably peptides and antigen targets may be conjugated to proteins and other moieties and delivered with adjuvants such as alum, squaline oil in water emulsion amino acids, proteins, carbohydrates and/or other adjuvants.

Another embodiment of the invention is directed to methods for treating or preventing drug-resistant MTB infection comprising administering an immunological composition containing antibodies and preferably monoclonal antibodies of the invention to a mammal. Preferably the antibodies are administered to a patient orally, intramuscularly, intravenously or subcutaneously and generates a humoral response in the mammal that comprises generation of antibodies specifically reactive against MTB moieties that impede host immunity or induce antibodies that enhance host immunity.

Another embodiment of the invention is directed to an immunological composition comprising antibodies and preferably monoclonal antibodies for the treatment or prevention of a latent infection of *Mycobacterium tuberculosis* (MTB) in a mammal. Mammals with latent infection may otherwise appear healthy, but still retain an MTB infection that often, although not always, is infectious to others. Antibodies of the invention are specifically reactive and bind one or more MTB epitopes that may be chemically or physically altered. Antibodies may be produced through recombinant techniques, such as humanization of murine antibodies preferably including a pharmaceutically acceptable carrier. Preferably the antibody-reactive antigen comprises an MTB surface secreted or intracellular antigen. Preferably the antigen comprises one or more of an MTB surface antigen, a synthetic MTB peptide, a synthetic composite peptide, or a combination thereof. Preferably the antibodies are specifically reactive against an MTB antigen wherein the MTB has been alcohol-killed, such as with ethanol, heat-killed, or gluteraldehyde-killed. The alcohol for example denatures the proteins and disassociates the lipid structures in the cell wall producing new and altered (non-natural) molecules. Preferably the pharmaceutically acceptable carrier comprises water, oil, fatty acid, carbohydrate, lipid, cellulose, or a combination thereof. Preferably peptides and antigen targets may be conjugated to proteins and other moieties and delivered with adjuvants such as alum, squaline oil in water emulsion amino acids, proteins, carbohydrates and/or other adjuvants.

Another embodiment of the invention is directed to methods for treating or preventing latent MTB infection comprising administering an immunological composition containing antibodies and preferably monoclonal antibodies of the invention to a mammal. Preferably the antibodies are administered to a patient orally, intramuscularly, intravenously or subcutaneously and generates a humoral response in the mammal that comprises generation of antibodies specifically reactive against MTB moieties that impede host immunity or induce antibodies that enhance host immunity.

Another embodiment of the invention is directed to methods for treating or preventing infection of drug-resistant *Mycobacterium tuberculosis* (MTB) or latent MTB infection in a mammal comprising administering to the mammal polyclonal or monoclonal antibodies that are specifically reactive against MTB moieties, such as mycolic acid that stimulate cellular phagocytic activity and destruction of MTB by phagocytes, enhances cytokine induced immunity to MTB or neutralizes toxic MTB substances, and/or cocktails of two or more monoclonal antibodies (MABs) that enhance immunity to MTB. Preferably, the anti-MTB antibodies are polyclonal antibodies or monoclonal antibodies and react against one or more MTB moieties.

Another embodiment of the invention is directed to monoclonal antibodies that are specifically reactive against mycolic acid of drug-resistant MTB. Preferably the monoclonal antibody is an IgA, IgD, IgE, IgG or IgM, and may be derived from most any mammal such as, for example, rabbit, guinea pig, mouse, human, fully or partly humanized, chimeric or single chain of any of the above. The DNA encoding the antibodies may be utilized in any appropriate cell line to produce the encoded MABs. Another embodiment comprises hybridoma cultures that produce the monoclonal antibodies. Another embodiment of the invention comprises non-naturally occurring polyclonal antibodies that are specifically reactive against mycolic acid of MTB.

Another embodiment of the invention is directed to methods for treating or preventing latent and/or drug-resistant MTB infection by administering a monoclonal or polyclonal antibody that is specifically reactive against mycolic acid of MTB.

Another embodiment of the invention is directed to methods for treating or preventing latent and/or drug-resistant MTB infection by administering to a patient an effective amount of BCG vaccine and further enhancing the effectiveness and/or the length of protection by also administering an effective amount of the vaccine of the invention that induces humoral immunity and provides enhanced phagocytic function. Enhanced phagocytic function by vaccine or antibody is defined as stimulated cellular phagocytic activity and enhanced destruction of the MTB bacillus inside the phagocyte.

Another embodiment of the invention is directed to methods of identifying one or more antibodies that activate phagocytizing cells, comprising: providing a microbe; generating antibodies that are specifically responsive to the microbe: incubating the generated antibodies with the phagocytizing cells; determining an activity of the phagocytizing cells after incubation with the antibodies; and selecting the one or more antibodies that increase the activity of the phagocytizing cells as compared to a control. Preferably the microbe is live or killed MTB and optionally, the microbe can be treated with one or more chemical and/or physical agents. Preferably the chemical agent is ethanol or gluteraldehyde. Also preferably, the antibodies generated from a mouse and preferably monoclonal antibodies. Phagocytizing cells include, but are not limited to macrophages, neutrophils, monocytes, mast cells, white blood cells, dendritic cells, phagocytic cell lines, HL-60 cells, U-937 cells, PMA treated cells, PMA treated U-937 cells, and combinations thereof. The activity of the cells can be determined, for example, by visual inspection, by antigen uptake, or fluorescent based microscopy assay of the phagocytizing cells. Preferably the phagocytizing cells show activity only on incubation with the one or more selected antibodies. Suitable controls include, for example, the phagocytic activity of the cells that have not been treated with any antibodies, the phagocytic activity of the cells after incubation with antibodies provided against untreated antigen, or the phagocytic activity of the cells after treatment with an agent that does not generate phagocytic activity. Preferably the one or more antibodies selected treat or prevent microbe infection of a mammal. Also preferable, the one or more antibodies selected are mouse antibodies that have been humanized for the prevention and/or treatment of a disease or disorder.

Other embodiments and advantages of the invention are set forth in part in the description, which follows, and in part, may be obvious from this description, or may be learned from the practice of the invention.

DESCRIPTION OF THE DRAWINGS

FIG. 1 Antisera titers from M3 1319-1324 (Immunized with MTB non-natural surface antigens on the altered surface of EtOH-k TB) on EtOH-k TB coating @ 1:1000.

FIG. 2 Antisera titers from M3 1325-1330 (Immunized with MTB non-natural surface antigens on the surface of Glut-k TB) on EtOH-k TB coating @ 1:1000.

FIG. 3 Antisera titers from M3 1331-1336 (Immunized with MTB non-natural antigens from Son. Glut-k TB) on EtOH-k TB coating @ 1:1000.

FIG. 4 Antisera titers from M3 1337-1342 (Immunized with MTB non-natural antigens from Son. Glut-k TB+adjuvant) on EtOH-k TB coating @ 1:1000.

FIG. 5 High level binding of isolated TB Pep01 (SEQ ID NO 1) at 1 μg/ml and 10 μg/ml to MS 1124 sera at 42 days, 112 days and prefusion.

FIG. 6 Hybridoma productivity from MS 1143 and 1147 fusion as measured on whole MTB (ethanol killed) and mycolic acid.

FIG. 7 Binding profiles of purified M1438 FE11 II B3 (alpha-TB Pep 02) to various antigens (SEQ ID NO. 7).

FIG. 8 Opsonophagocytic Mycobacterial killing assay; effect of MAB with HL60 cells and C1q.

FIG. 9 Blood clearance of MTB in Balb/c mice; effect of anti-MAB monoclonal antibodies.

FIG. 10 Absorbance values for 1417 spleen cell supernatants (1:5 dilution) treated with EtOH-killed TB±10 μg/ml of MAb AB9 1A5 in IFN-gamma assay.

FIG. 11 Absorbance values for 1418 spleen cell supernatants (1:5 dilution) treated with EtOH-killed TB±10 μg/ml of MAb AB9 1A5 in IFN-gamma assay.

FIG. 12 Effect of Mab AB9 1A5 (10 μg/ml) on induction of IL-4 in 1417 spleen cells by EtOH-killed TB.

FIG. 13 Effect of Mab AB9 1A5 (10 μg/ml) on induction of IL-4 in 1418 spleen cells by EtOH-killed TB.

DESCRIPTION OF THE INVENTION

Approximately one third of the world population is infected with *Mycobacterium tuberculosis* (MTB). Current treatment includes a long course of antibiotics and often requires quarantining of the patient. Resistance is common and an ever increasing problem, as is the ability to maintain the quarantine of infected patients. Present vaccines include BCG which is prepared from a strain of attenuated (virulence-reduced) live bovine tuberculosis bacillus, *Mycobacterium bovis*, and live non-MTB organisms. BCG carries substantial associated risks, especially in immune compromised individuals, and has proved to be only modestly effective and for limited periods. It is generally believed that a humoral response to infection by MTB is ineffective and optimal control of infection must involve activation of T cells and macrophages.

It has been surprisingly discovered that certain regions of MTB when chemically or physically altered from their natural state generate an enhanced immune response against MTB in mammals and, preferably, drug-resistant and/or latent MTB infections. Preferred alterations are created when the MTB is treated with chemicals such as, for example, ethanol, gluteraldehyde or another chemical that inactivates or kills the organisms. In contrast, antigens of or antibodies generated against these regions without alteration (e.g. BCG vaccine) do not produce a protective response even in adults with a robust immune system. These regions or epitopes that are created after treatment are referred to as immunity enhancing antigens (IEAs). These IEAs are recognized by the immune system of the host when administered to treat or prevent infection, by generating a cellular and/or humoral immune response to the infection. Without limiting the invention, the non-naturally occurring IEAs of the invention are believed to be unrecognized by the mammalian immune system due to physical changes created to the chemical structure of the antigen and/or by removal of one or more chemical moieties that otherwise block recognition of the epitope of the whole non-altered MTB or even of a degradation product of the MTB organism. On the isolation of an IEA, the physical or chemical alteration of one or more new epitopes are revealed to the host immune system generating a protective response against infection that is not otherwise available from a vaccine using whole or partial untreated organisms. Preferably, the IEAs of the invention are created from chemically killed organisms, such as ethanol killed, or degradation products of ethanol-killed organisms. IEAs of MTB include, but are not limited to epitopic regions of the surface of MTB, and various selected regions and sequences of the MTB components including, but not limited to MTB heat shock protein, peptidoglycan, mycolic acid and lipoarabinomannan (LAM). Preferred amino acid and nucleic acid sequences of the invention contain or encode one or more epitopes of an IEA for MTB, and/or additional epitopes specific for other infections such as, for example, a viral infection (e.g. influenza). Preferred IEAs of the invention include altered portions of peptidoglycan, mycolic acid and LAM, which are useful as peptide vaccines and/or peptide adjuvants. Nucleic acid sequences of the invention are preferably recombinantly produced and/or synthetically manufactured. Also preferred are nucleic acid aptamers and peptide aptamers and other molecules that mimic the structure and/or function of the non-natural antigens or antibodies of the invention. Also preferred are peptide and/or nucleic acid sequences that contain or encode one or more epitopes of an IEA antigen of another pathogen, such as, for example, a viral (DNA or RNA), bacterial, fungal or parasitic pathogen that is the causative agent of a disease (e.g., influenza, HIV/AIDS, hepatitis, lower respiratory infections, measles, tetanus, cholera, malaria, viral and/or bacterial meningitis, infections of the digestive tract, pertussis, syphilis). Combinations of epitopes from both MTB and other pathogens include, for example, peptide conjugates of MTB and influenza or another viral epitope, peptide conjugates of MTB with Diphtheria toxin (e.g. CRM), *Clostridium tetani* toxin and peptides and proteins, or another bacterial epitope, or peptide conjugates of MTB with *Plasmodium falciparum* or another parasitic epitope. Preferably, the peptide sequences of the invention (e.g. see Table 3, which includes peptide composites of MTB, peptide composites of influenza, and combined MTB-influenza composite peptides) are synthetic peptide vaccines that generate and/or enhance an immune response to a pathogenic infection such as, for example, MTB, influenza virus, or the etiological agents of cholera, malaria, leprosy, AIDS, and/or another infectious disease, and prevent and/or treat the disease and infection. Also preferably, the immune response generated is protective against the infection that shields individuals from infection outside of the geographical or time period of the limits of protection, for example, associated with the various BCG vaccines presently in use. Preferably, vaccines of the invention provide protection to the patient for greater than about one year, more preferably greater than about two years, more preferably greater than about three years, more preferably greater than about five years, more preferably greater than about seven years, more preferably greater than about ten years, and more preferably greater than about fifteen or twenty years.

Preferably the immune response generated upon the administration of a vaccine of the invention is protective against multi-drug resistant and/or latent TB or another infection and enhance and/or prime the immune system of the patient to be immunologically responsive to an infection such as by promoting recognition of the pathogen, a greater and/or more rapid immunological response to an infection, phagocytosis of the pathogen or killing of pathogen-infected cells, thereby promoting overall immune clearance of the infection, including latent TB infection and reactivation TB. Preferably, a vaccination of an infected mammal with an IEA of the invention promotes the activation of a humoral and/or cellular response of the mammalian immune system. For example, administering an IEA of the invention to an infected mammal promotes the sensing of the infection and then clears the infection, including latent infection, from the mammalian system by inducing or increasing phagocytic activity. Preferably this sensing and clearance activity is effective to clear the body of both active organisms and latent or dormant organisms and thereby prevent a later resurgence of the infection.

One embodiment of the invention is directed to vaccines of antibodies and/or antigens that, upon administration to a patient, provide for protection against infection of a pathogen. Vaccines containing IEAs are effective to stimulate a cellular and/or humoral response in a patient. Alternatively, the vaccine may stimulate a humoral response that will stimulate an enhanced cellular or phagocytic cell response to any invading pathogen such as MTB. Preferably the vaccines of the invention contain an MTB EIA such as, for example, one or more epitopes of altered peptidoglycan, mycolic acid, lipoarabinomannan (LAM), or a combination of one or more of these altered epitopes. Preferred MTB epitopes include MTB sequences and composites of MTB sequences plus other epitope sequence, such as those listed in Table 3.

Vaccines of the invention may contain one or multiple sequences and/or portions that are derived from the same or from different source materials or organisms. Source materials include, for example, proteins, peptides, toxins, cell wall components, membrane components, polymers, carbohydrates, nucleic acids including DNA and RNA, lipids, fatty acids, and combinations thereof. Vaccines with multiple portions derived from different sources are referred to herein as conjugate vaccines and may include portions derived from, for example, proteins and lipids, peptides and fatty acids, and lipids and nucleic acids. Vaccine conjugates may contain portions derived from distinct organisms, such as, for example, any combination of bacteria (e.g. MTB, Strep, Staph, Pseudomonas, *Clostridium*), virus (e.g., RNA or DNA viruses, influenza, HIV, RSV, Zika, poliomyelitis), fungal or mold, and parasite (e.g. malaria). These conjugates may be composed of, for example, a portion of mycolic acid of MTB coupled to serum albumin (e.g. bovine serum albumin or BSA). Exemplary conjugate vaccines include, but are not limited to conjugates of a surface protein of MTB, peptidoglycan, mycolic acid, or LAM with a protein such as tetanus toxin or diphtheria toxin.

Also preferred are vaccines of the invention that include one or more of a pharmaceutically acceptable carrier, diluent, excipient, adjuvant and/or other medicinal or pharmaceutical agent or preparation known to those skilled in the art. Preferred pharmaceutically carriers include one or more of water, fatty acids, lipids, polymers, carbohydrates, gelatin, solvents, saccharides, buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents or an immunological inert substance, and especially preferred are carriers designated as generally recognized as safe (GRAS) by the U.S. Food and Drug Administration or another appropriate authority.

Although the peptides of the invention may be complete vaccines against an infection in and of themselves, it has also been discovered that the peptide vaccines of the invention enhance the immune response when administered in conjunction with other vaccines against the same or a similar infection such as, for example, BCG against a TB infection. As a secondary vaccine or adjunctive treatment in conjunction with an existing primary vaccine treatment, secondary vaccines (which may be antibodies or antigens) of the invention provide a two punch defense against infection which is surprisingly effective to prevent or extend the period of protection available from the conventional primary vaccine. The primary vaccine (i.e., conventional vaccine) and secondary vaccines (vaccines of the invention) may be administered about simultaneously, or in staggered fashion in an order determined empirically or by one skilled in the art. Preferably the peptide vaccine is administered in advance of an attenuated or killed whole cell vaccine, but may also be administered after or simultaneously (e.g., collectively as a single vaccination or as separate vaccination compositions). Preferably the peptide vaccine is administered from between about two to about thirty days in advance or after administration of the whole cell vaccine, and more preferably from between about four to about fourteen days in advance or after. Without being limited as to theory, it is currently believed that the first vaccine primes the immune system of the subject and the second vaccine provides the boost to the immune system creating a protective immunological response in the patient.

Another embodiment of the invention comprises one or more antibodies that binds to one or more specific targets or pathogens, preferably one or more MTB epitopes that are IEAs of the invention optionally including one or more previously known epitopes. These antibodies, which may be either monoclonal or polyclonal, have surprisingly demonstrated antigen binding in ELISA assays to non-natural target MTB antigens, such as ethanol altered MTB, and demonstrate enhanced immune response to MTB and promote or enhance opsinization, phagocytic clearance, and/or killing of microorganisms such as MTB. Antibodies of the current invention that stimulate phagocytic function promote phagocyte activity to identify MTB, engulf the organism and then destroy the MTB bacilli. Antibodies enhance treatment, for example, by promoting phagocytosis of bacteria and clearance of the MTB from the blood. Antibodies of the invention have been developed to a number of antigen targets, including but not limited to mycolic acid of the surface of MTB, heat-shock proteins and other MTB antigens (e.g., 16 KD MTB heat-shock protein of SEQ ID NO 1).

Antibodies of the invention can be distinguished from naturally occurring antibodies by those of ordinary skill in the art. A number of techniques are available to distinguish existing from new antibodies and/or antigens. By way of example, antibodies of the invention can be reacted with an antigenic mix from, for example, MTB infected cell that had been previously bound with naturally occurring antibodies. What remains that becomes bound are the non-naturally occurring antibodies and the new antigens and epitopes. The newly bound antibodies can be isolated, identified, and characterized. The antibodies may bind to chemically or structurally altered epitopes or epitopes that become exposed after the chemical treatment. For example, natural MTB possesses biological material that prevents a host immune system from immunologically seeing and recognizing certain MTB antigens such as, for example, MTB proteins and lipids, peptides, fatty acids, polysaccharides, lipids and nucleic acids. Protein or peptide examples include, but are not limited to the heat-shock proteins, peptidoglycan, mycolic acid and lipoarabinomannan (LAM). Antibodies to one or more of these biological materials induce opsinization and/or killing on MTB microorganisms.

Another embodiment of the invention is directed to multiple antibodies of the invention (polyclonal, monoclonal or fractions such as Fab fragments, amino acid sequences of the variable binding antibody regions, single chains, etc.) that are combined or combined with conventional antibodies (polyclonal, monoclonal or fractions such as Fab fragments, single chains, etc.) into an antibody cocktail for the treatment and/or prevention of an infection. Combinations can include two, three, four, five or many more different antibody combinations with each directed to a different antigen including IEAs of the invention.

Antibodies to one or more different antigens or IEAs of the invention may be monoclonal or polyclonal and may be derived from any mammal such as, for example, mouse, rabbit, pig, guinea pig, rat and preferably human. Polyclonal antibodies may be collected from the serum of infected or carrier mammals (e.g., typically human, although equine, bovine, porcine, ovine or caprine may also be utilized) and preserved for subsequent administration to patients with existing infections. Administration of antibodies for treatment against infection, whether polyclonal or monoclonal, may be through a variety of available mechanisms including, but not limited to inhalation, ingestion, and/or subcutaneous (SQ), intravenous (IV), intraperitoneal (ID), and/or intramuscular (IM) injection, and may be administered at regular or irregular intervals, or as a bolus dose.

Monoclonal antibodies to one or more IEAs of the invention may be of one or more of the classes IgA, IgD, IgE, IgG, or IgM, containing alpha, delta, epsilon, gamma or mu heavy chains and kappa or lambda light chains, or any combination heavy and light chains including effective fractions thereof, such as, for example, single-chain antibodies, isolated variable regions, isolated Fab or Fc fragments, isolated complement determining regions (CDRs), and isolated antibody monomers. Monoclonal antibodies to IEAs may be created or derived from human or non-human cells and, if non-human cells, they may be chimeric MABs or humanized. Non-human antibodies are preferably humanized by modifying the amino acid sequence of the heavy and/or light chains of peptides to be similar to human variants, or genetic manipulation or recombination of the non-coding structures from non-human to human origins. The invention further comprises recombinant plasmids and nucleic acid constructions used in creating a recombinant vector and a recombinant expression vector the expresses a peptide vaccine of the invention. The invention further comprises hybridoma cell lines created from the fusion of antibody producing cells with a human or other cell lines for the generation of monoclonal antibodies of the invention.

Antibodies to IEAs and other substances when recognized by the immune system, promote phagocytosis and clearing of an infection caused by that microorganism prevent the establishment of a disease process. Pretreatment or simultaneous treatment of MTB with certain antibiotics exposes immune enhancing antigens of the microorganism to cell killing mechanisms of the immune system including, but not limited to phagocytosis, apoptosis, macrophage and natural-killer cell activation, cytokine and T-cell modulation and complement-initiated cell lysis.

Another embodiment of the invention is directed to methods for administering to a patient a composition containing antibodies of the invention and, preferably, with a pharmaceutically acceptable carrier. Antibodies to IEAs of a microorganism, either or both as polyclonal antibodies or monoclonal antibodies or cocktails of one or more antibodies, may be administered individually and/or in combinations with each other and/or other vaccines and/or treatments or preventions of the microorganism infection. Antibodies to immune enhancing antigens or other targets may be administered prophylactically prior to possible infection, or to treat an active or suspected MTB infection. Many MTB strains are or are becoming multi-drug resistant (MDR) or extensively drug resistant (XDR). MAbs of the invention can be used to promote immune clearance and killing of MTB strains that are resistant to antibiotics.

Another embodiment of the invention is directed to the prophylactic administration of MTB antibodies, or antigen in the form of a vaccine, to protect health care workers who administer to TB patients and, in particular, patients with multi or extreme drug resistant MTB infections. At present, a health care professional, or most anyone, who treats or cares for a patient infected with multi-drug resistant or extreme-drug resistant TB is at extreme risk for acquiring the same infection as those he or she cares for. There is also a substantial risk to all persons within a general health care facility that such a TB infection will be acquired by other health care workers at the facility or visitor who otherwise have no contact or interaction with such patients. With the prophylactic administration of antibodies or vaccines of the invention to health care workers, they are able to care for and attend these patients. With the administration of immunogenic compositions of the invention, preferably monoclonal antibodies or vaccines, a health care worker may be protected from nosocomial and occupationally acquired TB infection for weeks, months and longer.

Preferably the vaccine of immune enhancing antigens and/or antibodies to immune enhancing antigens of the invention is administered in conjunction with conventional vaccines against MTB (e.g., BCG) or as a Prime Boost with another vaccine such as, for example BCG. This combined vaccine of the invention provides an enhancement of the immune response generated and/or extends the effectiveness and/or length of period of immunity. Enhancement is preferably an increase in the immune response to MTB infection such as an increase in the cellular or humoral response generated by the host's immune system. An effective amount of vaccine, adjuvant and enhancing antigen of the invention is that amount which generates an infection clearing immune response or stimulates phagocytic activity. Upon administration of the combined vaccine, an increase of the cellular response may include the generation of targeted phagocytes, targeted and primed natural killer cells, and/or memory T cells that are capable of maintaining and/or promoting an effective response to infection for longer periods of time than the conventional vaccine would provide alone. An increase in the humoral response may include the generation of a more diverse variety of antibodies including, but not limited to different IgG isotypes or antibodies to more than one microbe or more than one MTB molecule that are capable of providing an effective response to prevent infection by MTB and/or another microbe as compared to the humoral response that would be generated from just a conventional MTB vaccine. Administration preferably comprises combining BCG vaccine and a vaccine antigen that generates a humoral response in the patient to a surface antigen of MTB. Preferably the response is to mycolic acid, peptidoglycan, lipoarabinomannan and/or another component of the microorganism, preferably one that presents or is otherwise exposed on the surface of MTB or secreted during infection. Some substances produced by MTB may be toxic to the host immune system or impede immune function. Antibodies that clear or neutralize these toxic substances (such as released or free mycolic acid components) can further act to enhance and improve host immunity.

Exposure of these MTB antigens to the antibodies of the invention or of the immune system of the patient may be augmented or substantially increased by prior or about simultaneous treatment with individual or combinations of antibiotics, cytokines and other bactericidal and/or bacteriostatic substances (e.g., substances that inhibit protein or nucleic acid synthesis, substances that injury membrane or other microorganism structures, substances that inhibit synthesis of essential metabolites of the microorganism), and preferably one or more antibiotic or substance that attacks the cell wall structure or synthesis of the cell wall of the microorganism. Preferably, the antibiotics do not cause the release of cell surface antigens, but expose antigens that are not otherwise exposed or easily accessible to the immune system. Effective amounts of antibiotics are expected to be less than the manufacture recommended amount or higher dose, but for short periods of time (e.g. about one hour, about 4 hours, about 6 hours, less than one or two day). Examples of such antibiotics include, but are not limited to one or more of the chemical forms, derivatives and analogs of penicillin, amoxicillin, augmentin, polymyxin B, cycloserine, autolysin, bacitracin, cephalosporin, vancomycin, and beta lactam. Antibiotics work synergistically with the immune enhancing antigens of the invention to provide an efficient and effective preventative or treatment of an infection. The antibiotics are not needed in bacteriostatic or bactericidal quantities, which is not only advantageous with regard to expense, availability and disposal, these lower dosages do not necessarily encourage development of resistance to the same degree, together a tremendous benefit of the invention. Preferably, the antibiotic is administered initially to damage and alter the pathogen cell wall and epitopes (for example to produce a non-natural surface and expose cell wall components such as mycolic acid non-natural epitopes and other moieties that can be recognized by the patient's immune system), followed a short time later with the antibody treatment, so that the IEA is more fully accessible to the antibody when administered. The period of time between treatment may be one hour or more, preferably 4 hours or more, preferably 8 hours or more, or preferably 12 or 24 hours or more.

Antibodies to immune enhancing antigens of the invention may be administered directly to a patient to treat or prevent infection of MTB via inhalation, oral, SQ, IM, IP, IV or another effective route, often determined by the physical location of the infection and/or the infected cells. Treatment is preferably one in which the patient does not develop or develops only reduced symptoms (e.g., reduced in severity, strength, period of time, and/or number) associated with MTB infection and/or does not become otherwise contagious. Antibodies used alone or in conjunction with anti-MTB antibiotics will increase the clearance of MTB from the blood or other tissues, or inactivate substances that impede immunity as measured by a more rapid reduction of symptoms, more rapid time to smear negativity and improved weight gain and general health. In addition, treatment provides an effective reduction in the severity of symptoms, the generation of immunity to MTB, and/or the reduction of infective period of time. Preferably the patient is administered an effective amount of antibodies to prevent or overcome MTB infection alone or as adjunctive therapy with antibiotics.

Another embodiment of the invention is directed to methods of identifying one or more antibodies that promote phagocytosis and killing of mycobacteria. These methods comprise screening a population of antibodies and selected the one or more antibodies of those screened that are effective in the activation of phagocytizing cells. As a first step, microbes of interest are provided and may be purified, isolated or both. The microbes may be killed, attenuated or live microorganisms. Preferred microbes include MTB *Mycobacterium smegmatis* (MS), or another microorganism. Optionally, the microbe may be treated with a chemical or physical agent and preferred treatment include, for example, exposure to a chemical such as ethanol or gluteraldehyde that alters the chemical structure of one or more antigens of the microbe, or physical that alters the microbe structure. Alteration can involve a chemical change, such as, for example, removal or alteration of a specific chemical moiety, or physical such for example a shifting of a moiety so that a new region or epitope appears. The antibodies to be screened in the methods of the invention can be created or generated, or commercially provided. Preferably the antibodies are polyclonal antibodies, antibody fragments such as, for example, Fab, Fc and single chain antibodies, or monoclonal derived from humans, mice or another mammal. The antibodies are next incubated with deleted phagocytizing cells under conditions whereby the activity of the cells can be measured during or after a set period of incubation. Activity can be any cellular activity such as, for example, proliferation, the presence or absence of a marker, oxygen uptake or utilization, or determining any cellular activity such as, cytokine secretion or preferably, phagocytosis and killing of the microbe. Phagocytizing and cytokine secreting cells include many cells for example, macrophages, neutrophils, monocytes, mast cells, white blood cells, spleen cells, dendritic cells, phagocytic cell lines, HL-60 cells, U-937 cells, DMSO or PMA treated cells, PMA treated U-937 cells, and combinations thereof. The measurement of activity can be performed by any technique known to those skilled in the art and is preferable by observation of the cells, by the appearance of cell vacuoles, by microbe or antigen uptake assays, or by measurement of phagocytizing markers. Preferably the measurement of activity is performed using a fluorescent-based microscopy assay or microbial killing by the phagocyte. Upon determining activity of phagocytizing cells incubated with the antibodies, one or more of the antibodies that showed activity or an increased activity as compared to a control are selected. Controls include, for example, phagocytic activity of the cells that have not been treated with any antibodies, the phagocytic activity of the cells after incubation with antibodies provided against untreated antigen, or the phagocytic activity of the cells after treatment with an agent that does not generate phagocytic activity. Preferably the activity is enhanced after incubation with antibodies that specifically bind to the microbe or a microbial substance. Selected antibodies are preferably useful for the treatment and/or prevent of infection of the microbe. Preferably, when the microbe is MTB, the one or more antibodies that show increased activity of phagocytizing cells, such as phagocytosis and microbial killing as compared to a control can be used to treat and/or prevent MTB infection in a human or other mammal.

Although the invention is generally described in reference to human infection by *Mycobacterium tuberculosis*, as is clear to those skilled in the art the compositions including many of the antibodies, tools and methodology is generally and specifically applicable to the treatment and prevention of many other diseases and infections in many other subjects (e.g., cats, dogs, pets, etc.) and most especially diseases wherein the causative agent is of viral, bacterial, fungal and parasitic origins.

The following examples illustrate embodiments of the invention, but should not be viewed as limiting the scope of the invention.

EXAMPLES

Example 1

Mice bleeds: Female Balb/c mice were acquired at 3-4 weeks of age; 7-14 days prior to the commencement of the study to allow them acclimate to the facility. Thereafter, the mice were tagged with ear tags for identification, and bled at the orbital lobe prior to immunization to have a reference point. The mice were bled at days 20, 29, 63, and prior to fusion. About 150 μL-200 μL of blood was collected at each bleed. Antisera Titers for MS 1319-1342 Immunized with Washed Battelle Bugs (Batch III @ OD 600 nM=1.000).

Sera processing: At each bleed, blood was collected in micro-centrifuge tubes and stored in cryo-vials at from 2-8° C. overnight. On the next day, samples were centrifuged at 2000 rpm for 10 minutes at 22° C. The top layer of sera was carefully collected, avoiding red blood cells (RBC), and stored in new micro-centrifuge tubes at minus 20° C. In the event that the sera could not be processed the next day, sera samples were processed on the same day as the bleed. Sera samples were placed in a 37° C. incubator for 30 minutes, and then placed at 2-8° C. for 15 minutes. Afterwards, sera samples were centrifuged and processed in the manner indicated above. Sera processing was performed on the bench-top.

Killed MTB organisms: *M. tuberculosis* were grown in Middlebrook broth, washed three times in PBS and then suspended in either 70% ethanol or 2% glutaraldehyde activated with sodium bicarbonate. A third antigen preparation was sonicated (Son), glutaraldehyde killed MTB. Washed ethanol-killed and glutaraldehyde-killed MTB were obtained from Battelle at a concentration of $5.0\times10^{8}$ CFU/mL. TB Pep 01 was produced by Pi Proteomics at a purity of over 90%.

Mice Immunizations:

Whole Bug Immunizations: Tuberculosis bacterial, strain Battelle (Batch III), killed with ethanol (EtOH-k) or glutaraldehyde (Glut-k), were washed in PBS to remove potential toxic substances. One mL of antigen at original concentration was centrifuged at 12,000 rpm for 10 minutes. 900 μL of the supernatant was discarded and the pellet re-suspended 900 μL of PBS by centrifugation at 12000 rpm for 10 minutes. This was repeated two more times for a total of three washes. PBS was used because it is isotonic to blood and does not cause hardship to the mice.

Adjuvant Immunizations: 50% Alum and Titer-Max Gold (adjuvant). For the groups with adjuvant Titer-Max Gold, the adjuvant comprised 60% of the injection. Antigen was added to the adjuvant in a double plunger glass syringe where the emulsion was prepared. The mice were immunized at day 0 and boosted on Day-22, and within the week prior to fusion. Each mouse was immunized with 200 μL of antigen at varying concentrations to assess immunogenicity. The immunizations were delivered subcutaneously, and then intravenously prior to fusion. Enzyme-Linked Immunosorbent Assay (ELISA): The sera and supernatants (from hybridoma cells) were tested by ELISA to determine antisera and hybridoma titers.

Fusion and Hybridoma Production: Post-Day 63, mice that had been identified by ELISA for high antisera titers were sacrificed and their spleens harvested. The spleen cells were fused to SP2/0 myeloma cells using ethylene glycol, and 100 µl seeded and grown in sterile, 96-well culture plates as adhesion cells. The fused cells were stored in a 37° C. humidified 5% $CO_2$ incubator. The fusion was performed in a sterile laminar flow hood.

Cell Culture: On Day 1, the day after fusion, 1×HAT selection media was introduced to select for hybridoma cells. The cells were incubated at 37° C. in a humidified 5% $CO_2$ incubator. On Day 9 or 10, they hybridoma supernatants were tested for antibody production. Afterwards, cells were fed twice a week, on Mondays and Fridays with hybridoma media that consisted of 15% FBS, 1% L-Glutamine, 0.1% Gentamycin, 1% Protein-free hybridoma media, and 1×HT media in DMEM. For each re-feed; 60 µl of supernatant were discarded and 100 µl of media added to each well. This process was performed using aseptic techniques in a sterile hood. Refer to SOP-1005-00 Basic Cell Culture Techniques.

Mycolic Acid-BSA Conjugation:

Reagents: Mycolic acid from *mycobacterium tuberculosis*, Sigma Cat: M4537. N-hexane, Sigma Cat: 296090. 1-(3-Dimethylaminopropyl)-3-ethylcarbodiimide Hydrochloride, TCI Cat: D1601. DMSO, Sigma Cat: D2650. Bovine serum albumin, Sigma Cat: A9418.

Method: 1.2 mg of mycolic acid was dissolved into 25 µL of n-hexane. 1.7 mg of BSA was dissolved into 1.2 mL of 0.1M MES buffer pH 6, and 0.06 mL of DMSO was added with vortexing. The mycolic acid solution was added slowly to the BSA solution with vortexing. 14 mg of EDC was added as dry powder with stirring. The pH was recorded to be 5.5 after all additions and the reaction proceeded overnight at 4° C. The following day the conjugate solution was dialyzed against PBS-T in 14 k MWCO tubing.

TB Peptide—Conjugation:

CRM-Flu Peptide 5906 (NS0243), CRM-TB peptide 1 (Pep01) (NS0245), CRM-TB peptide 2 (Pep02) (NS0246) (see Table 1): CRM was brought to 6 mg/mL in 0.1M HEPES pH 8+0.1% Tween 80. A 30 fold excess of 0.2M SBAP in DMSO was added while vortexing and incubated at room temperature for 1 hour. Following incubation, the CRM was dialyzed against PBS-EDTA pH 7.7. All peptides were dissolved in 0.1M HEPES pH 8 at 10 mg/mL. A two fold molar excess of 0.2M SATA in DMSO was added while vortexing and the solutions incubated at room temperature for one hour. The solutions were brought to pH 6 with 1M sodium acetate and 1M $NH_2OH$ was added to a final concentration of 50 mM. The CRM-SBAP was taken out of dialysis and divided into 3×3 mg aliquots. The peptides were added to the CRM-SBAP while vortexing and the pH brought to 8 with 1M HEPES pH 8. The conjugates were allowed incubate overnight at 4° C. The conjugates were dialyzed against PBS pH 8, put through a 0.2 µm filter, and the A280 was read for concentration using 1.07 as the 0.1% extinction coefficient of CRM. CRM-Mycolic acid (NS0244): CRM was brought to 6 mg/mL in 0.1M HEPES pH 8+0.1% Tween 80. 5 mg of mycolic acid dissolved into 100 µL of n-hexane. The CRM (3 mg) and 2 mg of mycolic acid were mixed and 50 mg of EDC was added. The solution had a final pH of 7.9 and incubated overnight at 4° C. The conjugate dialyzed into PBS pH 8, filtered to 0.2 µm, and the concentration was determined by A280.

TABLE 1

|  | NS0243 | NS0244 | NS0245 | NS0246 |
|---|---|---|---|---|
| CRM Used | 3 mg | 3 mg | 3 mg | 3 mg |
| Peptide Used | 3.6 mg | 2 mg | 4.5 mg | 3.2 mg |
| Final OD | 2.3 | 0.64 | 2.4 | 1.84 |
| Final Concentration | 2.15 mg/mL | 0.6 mg/mL | 2.24 mg/mL | 1.72 mg/mL |

Reagents: Tetanus toxoid obtained from the Serum Institute, Batch 031L1006. Diphtheria toxoid (CRM) was obtained from Fina Biosolutions, Rockville, Md. DMSO, Sigma Cat: D2650. N-Succinimidyl 3-(2-pyridyldithiol)-propionate (SPDP), Molecular BioSciences Cat: 67432. 4-Maleimidobutyric aced NHS-ester (GMBS), Molecular BioSciences Cat: 98799. TB Peptide, PiProteomics, Name Peptide 1 (SEQ ID NO 1; the 16 KD heat-shock MTB antigen "Promiscuous Peptide") (Gowthaman et al., JID 204: 1328-1338, 1 Nov. 2011). Dithiothreitol, Spectrum Cat: DI184. 0.8 mg of peptide was diluted into 80 µL of 0.1M HEPES pH 8 and 19 µL of 0.1M SPDP in DMSO was added with vortexing. In a separate vial, 5 mg of BSA was diluted into 0.48 mL of 0.1M HEPES pH 7.4 and 7 µL of 0.1M GMBS in DMSO was added with vortexing. Both solutions were incubated at room temperature for 1 hour. The BSA-GMBS was dialyzed against 2 L of PBS-EDTA pH 6.8. 1M DTT in NaOAc was added to the peptide solution to a final concentration of 15 mM and incubated for 1 hour. The peptide was desalted on a P2 column with PBS-EDTA pH 6.8 and 0.2 mL fractions were collected. The fractions were checked for 280 nm absorbance and the first half of the curve with 280 OD were pooled and added to the BSA-GMBS. The solution was allowed to react overnight at 4° C., followed by dialysis into PBS.

Example 2: Induction of Humoral Immunity

Figure 2:
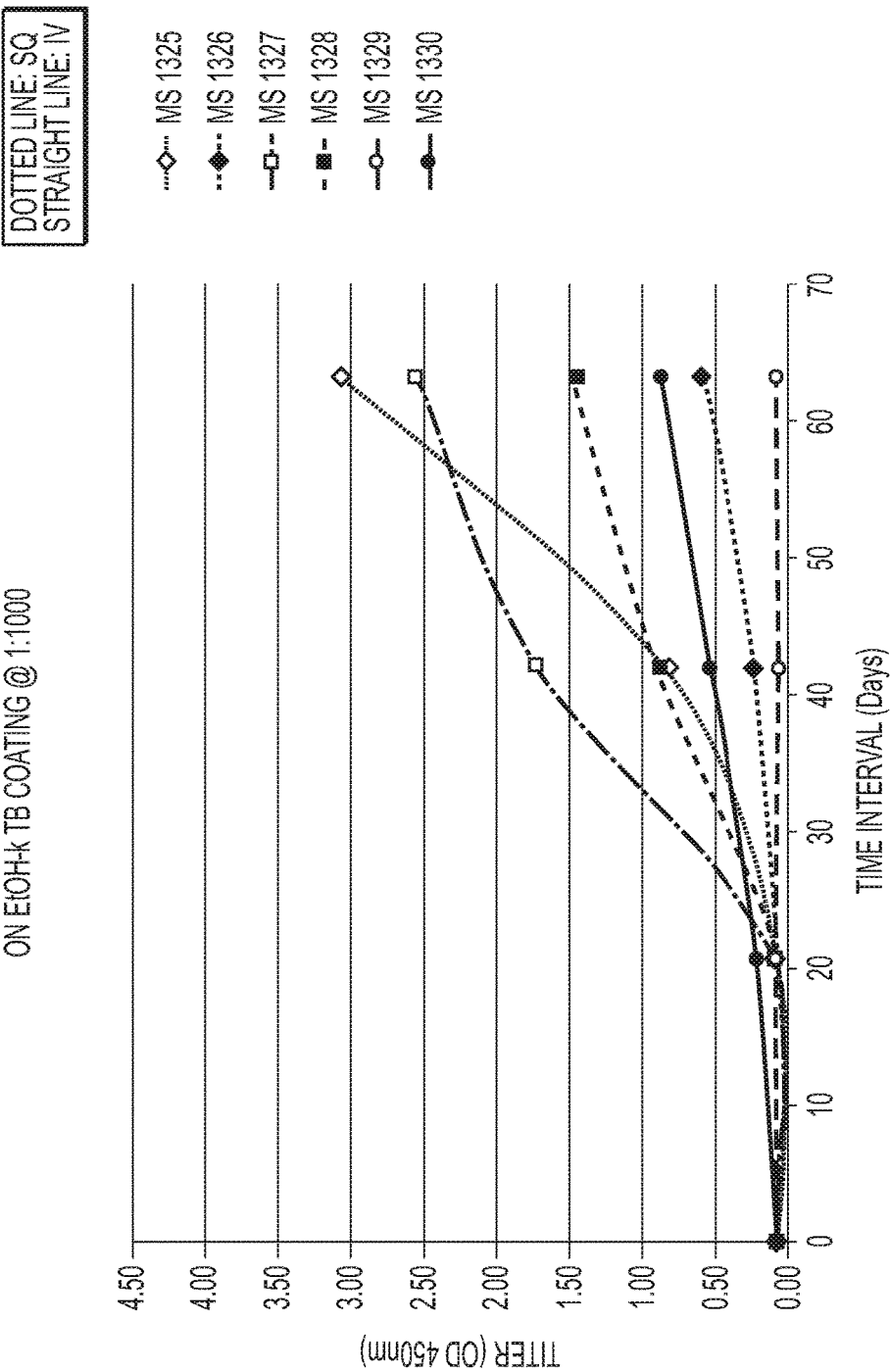
Figure 3:
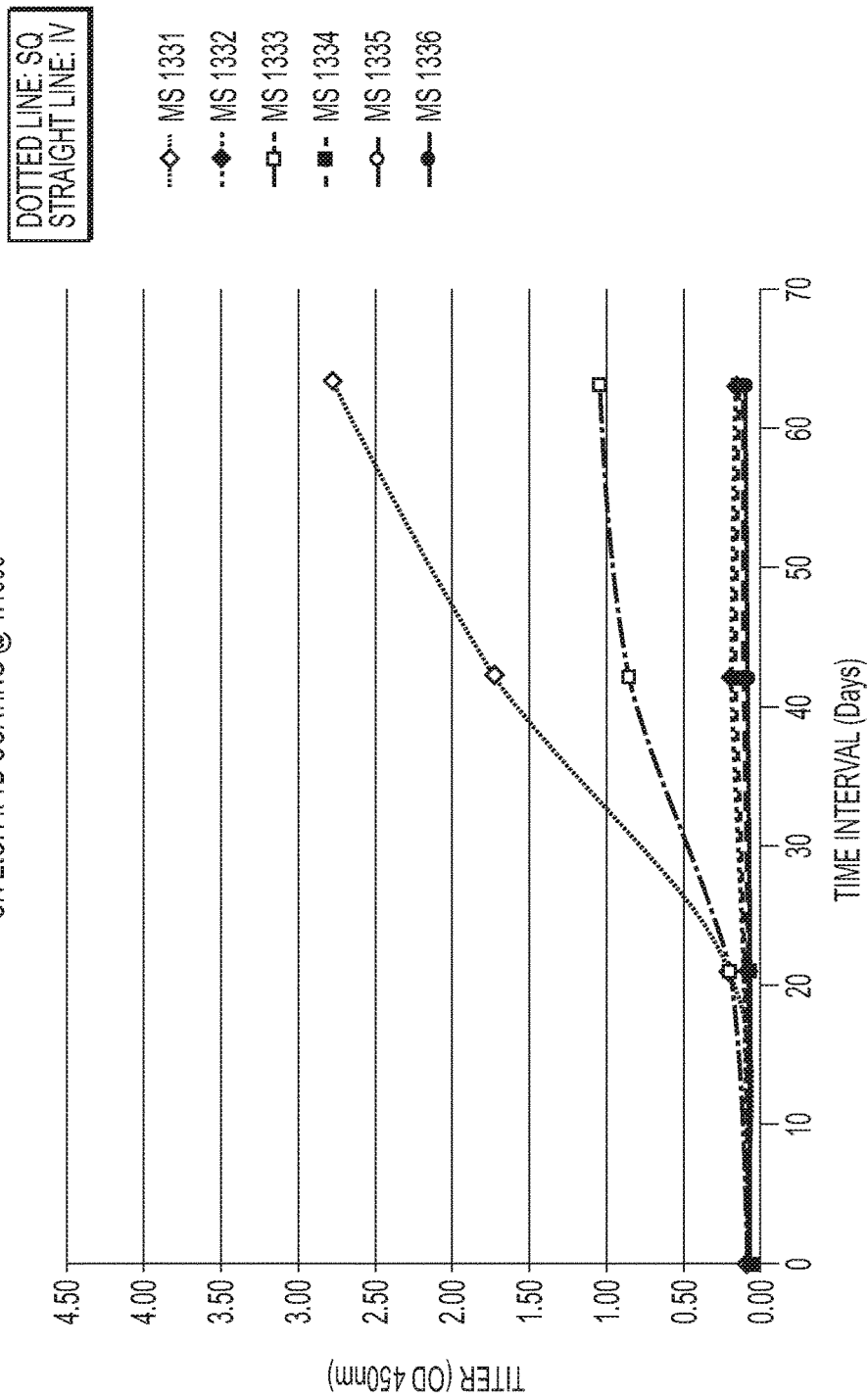
Figure 4:
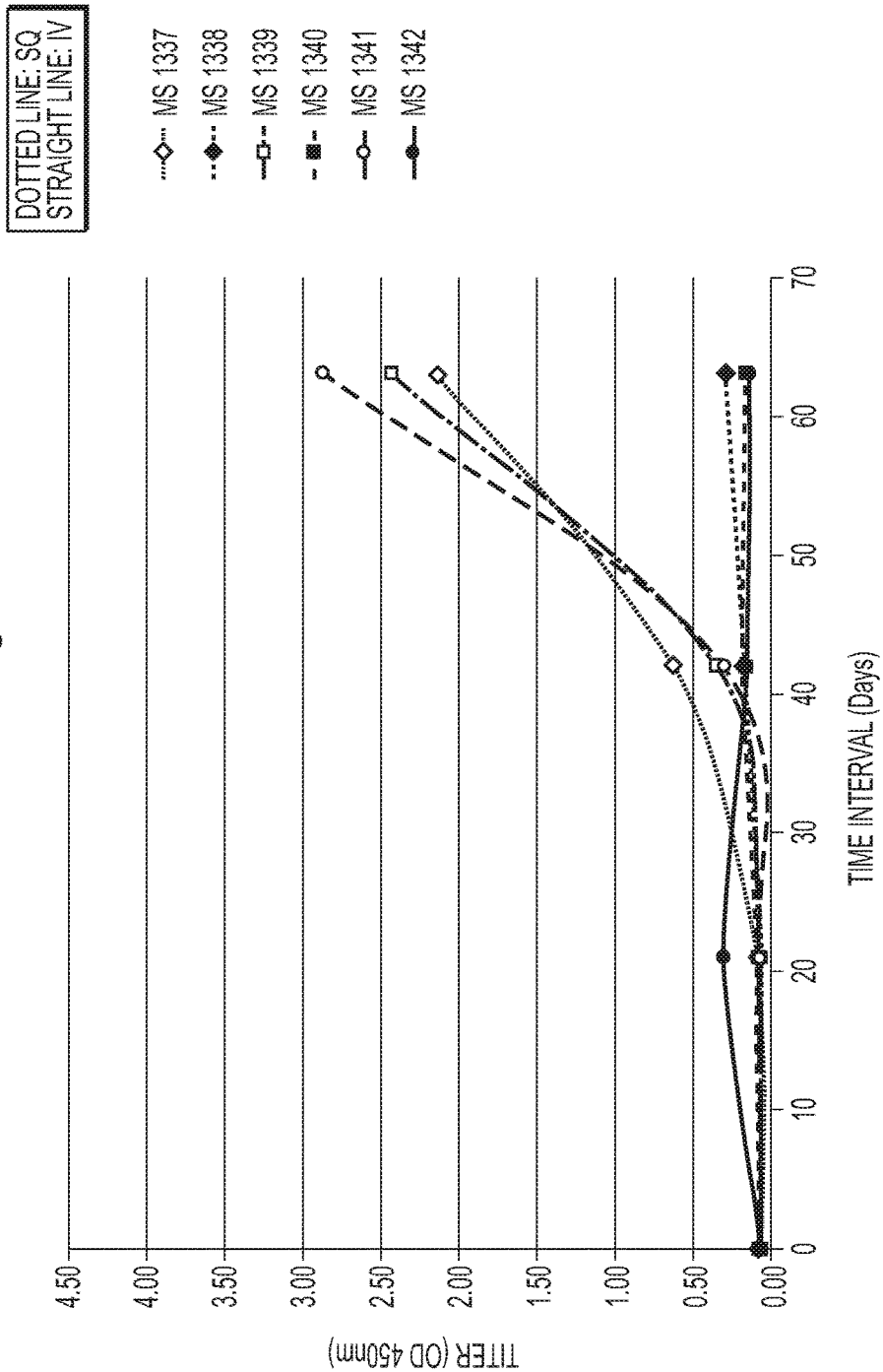
Figure 5:
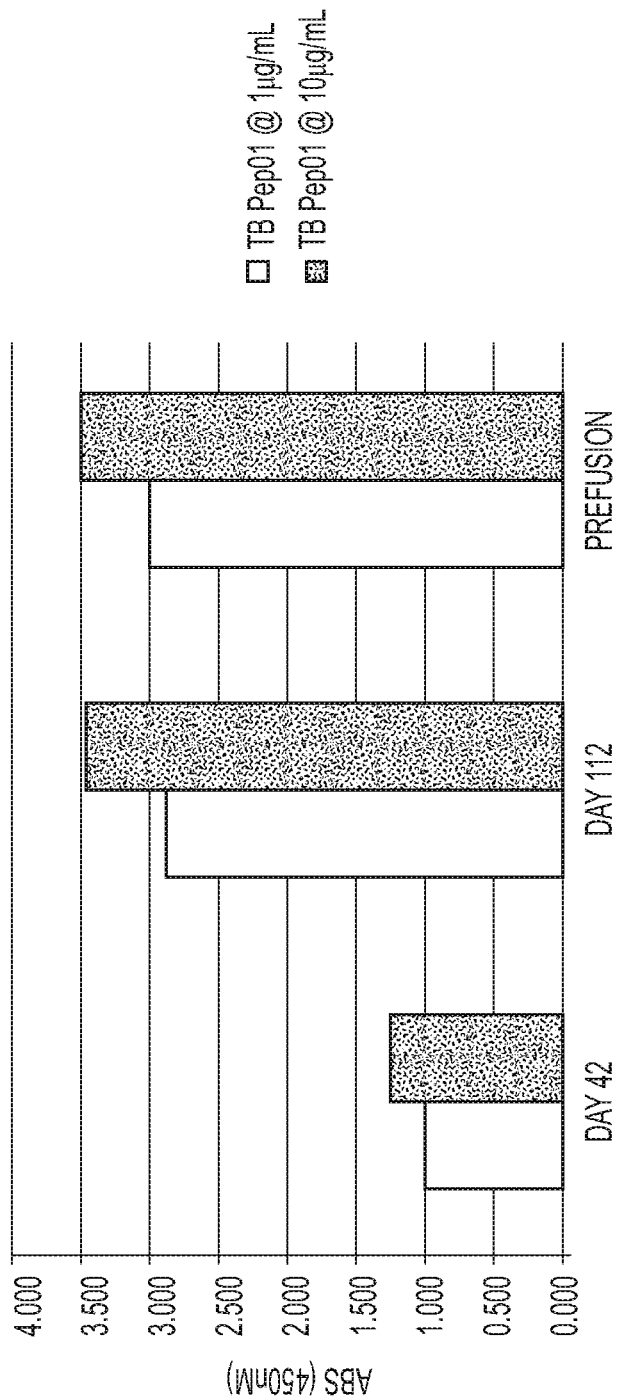
Figure 6:

Mice immunized with MTB killed with ethanol (FIG. 1) or glutaraldehyde (FIG. 2) developed a strong humoral antibody response with good binding to MTB. In addition, mice immunized with ethanol-killed MTB had a higher and more rapid rise in antibody titers than did mice immunized with Glut-killed MTB and SQ was superior to the IV route of immunization. Mice immunized SQ with sonicated MTB (FIG. 3) had increased antibody responses compared to IV and adjuvant, Alum and Tmax (squalene, water oil emulsion) (FIG. 4), enhanced antibody to MTB in some mice. A summary of the results from these experiments is provided in Table 2.

TABLE 2

ELISA Results

| Sample | Route | Mouse ID | Prelim | Day 21 | Day 42 | Day 63 |
|---|---|---|---|---|---|---|
| EtOH + TB | SQ | 1319 | 0.076 | 0.276 | 4.000 | 4.000 |
|  | SQ | 1320 | 0.074 | 0.763 | 3.812 | 4.000 |
|  | SQ | 1321 | 0.076 | 0.519 | 4.000 | 4.000 |
|  | IV | 1322 | 0.063 | 1.553 | 3.346 | 3.611 |
|  | IV | 1323 | 0.066 | 1.857 | 4.000 | 4.000 |
|  | IV | 1324 | 0.072 | 0.164 | 0.834 | 1.578 |
| Glu + TB | SQ | 1325 | 0.072 | 0.074 | 0.840 | 3.051 |
|  | SQ | 1326 | 0.062 | 0.060 | 0.272 | 0.588 |
|  | SQ | 1327 | 0.076 | 0.102 | 1.751 | 2.573 |
|  | IV | 1328 | 0.064 | 0.071 | 0.907 | 1.481 |
|  | IV | 1329 | 0.094 | 0.081 | 0.106 | 0.135 |
|  | IV | 1330 | 0.086 | 0.240 | 0.561 | 0.915 |
| Son/Glu + TB | SQ | 1331 | 0.085 | 0.193 | 1.722 | 2.752 |
|  | SQ | 1332 | 0.077 | 0.094 | 0.190 | 0.155 |

TABLE 2-continued

ELISA Results

| Sample | Route | Mouse ID | Prelim | Day 21 | Day 42 | Day 63 |
|---|---|---|---|---|---|---|
| | SQ | 1333 | 0.090 | 0.210 | 0.854 | 1.037 |
| | IV | 1334 | 0.068 | 0.077 | 0.152 | 0.127 |
| | IV | 1335 | 0.080 | 0.077 | 0.097 | 0.096 |
| | IV | 1336 | 0.062 | 0.070 | 0.085 | 0.135 |
| Son/Glu + TB + | SQ | 1337 | 0.064 | 0.112 | 0.628 | 2.128 |
| Adjuvant | SQ | 1338 | 0.078 | 0.067 | 0.169 | 0.280 |
| | SQ | 1339 | 0.071 | 0.096 | 0.356 | 2.422 |
| | IV | 1340 | 0.092 | 0.101 | 0.185 | 0.149 |
| | IV | 1341 | 0.087 | 0.086 | 0.299 | 2.843 |
| | IV | 1342 | 0.066 | 0.308 | 0.156 | 0.134 |

Mice immunized with ethanol killed TB had the best response and there was little difference observed between immunizations SQ or IV. At day 21 there was a significant difference in titers of SQ and IV immunizations. By day 42 and day 63, there was little to no difference. Glutaraldehyde-killed TB mice developed titers, but not until day 42 as there appeared to be a delay to the immune response. Sonication was thought to increase the availability of epitopes, but only 1331 and 1333 (both SQ) developed titers at day 42 with an increase at day 63. Although adjuvant is supposed to increase activity of the immune system, the group with adjuvant had only modestly elevated titers at day 63. One possibility is that the epitopes did not respond effectively with this type of adjuvant.

A strong binding to mycolic acid was demonstrated in post immunization sera and further studies showed that when spleen cells were fused, the majority of MABs bound to MTB and mycolic acid. Mycolic acid impedes opsonophagoctosis and vaccines that induce humoral immunity to this cell wall component or antibodies that bind to this lipid would be useful to prevent or treat TB. A mycolic acid subunit vaccine or conjugate vaccine that induces humoral immunity to MTB would be useful to prevent or mitigate TB infections.

Peptide Conjugate Vaccine

Mice immunized with a small TB peptide conjugate vaccine (SEQ ID NO 1) developed humoral immunity to this 16 KD heat shock protein. These antibodies to an important TB moiety provide another method for humoral immune induction to mitigate against TB infection, either alone or with other antibodies raised against one or more other key targets, such as mycolic acid. The 16KD heat shock protein maybe critical for MTB persisting in phagocytes and a vaccine or passive IgG therapy might prevent or treat latent TB.

Example 3: Immunizations

Mouse 1124 was immunized with TB heat shock peptide-BSA conjugate vaccine (100 µg) on days 0, 21, 42 and 112. On day 152 (3 days before sacrifice for splenic fusion), 6 logs of MTB that were ethanol killed were injected IV. Priming with MTB peptides followed by whole MTB challenge elicits a rapid rise to the priming peptide that can be detected within 3 days (FIG. 5).

It is surprising that the titers were higher within 3 days of challenge with whole killed MTB. Also, although small, priming with MTB peptides followed by whole MTB challenge elicited a rapid rise to the priming peptide that could be detected within 3 days.

Example 4: Hybridomas

Mice immunized with unwashed, ethanol killed MTB (as above), produced numerous hybridomas producing antibodies that bound to whole ethanol killed MTB (FIG. 6). Surprisingly there was a close correlation between serum binding to Mycolic acid and MTB bacilli. This killed MTB immunization produced a humoral immune response to mycolic acid and MTB, thus demonstrating that the polyclonal and monoclonal antibodies to mycolic acid, prepared according to the invention, can be useful for prevention and also treatment of MTB infections.

Example 5: Peptide Sequences

All peptides were synthetically manufactured. A listing of the sequences and the epitopes contained within each peptide is shown in Table 3 (Flu=influenza virus).

TABLE 3

| Sequences of Peptides of Vaccines |
|---|
| SEQ ID NO 1 SEFAYGSFVRTVSLPVGADE-TB Pep01 |
| SEQ ID NO 2 GNLFIAP (Flu HA epitope) |
| SEQ ID NO 3 HYEECSCY (Flu NA epitope) |
| SEQ ID NO 4 WGVIHHP (Flu HA epitope) |
| SEQ ID NO 5 GNLFIAPWGVIHHPHYEECSCY (composite of Flu HA plus NA sequences) |
| SEQ ID NO 6 WGVIHHPGNLFIAPHYEECSCY (composite of Flu HA plus NA sequences) |
| SEQ ID NO 7 SEFAYGSFVRTVSLPVGADEGNLFIAPWGVIHHPHYEECSCY-TB Pep02 (composite of HSPX with Flu HA, HA and NA sequences) |
| SEQ ID NO 8 GNLFIAPWGVIHHPHYEECSCYSEFAYGSFVRTVSLPVGADE (composite of Flu sequences of HA HA and NA with HSPX |
| SEQ ID NO 9 HYEECSCYSEFAYGSFVRTVSLPVGADE (composite of Flu NA with HSPX) |
| SEQ ID NO 10 SEFAYGSFVRTVSLPVGADEHYEECSCY (composite of Flu NA with HSPX) |

Mice were immunized with ethanol killed MTB and MTB conjugate vaccine CRM-TB Pep01 according to standard protocol. The mice developed brisk antibody titers to TB Pep01, mycolic acid, and other surface antigens as measured by ELISA (see Figures). Monoclonal antibodies were produced according to protocol, characterized and purified. Isolated MABs from mice immunized with ethanol killed MTB were generally type IgG1 while the conjugate CRM—Pep01 vaccine MABs were each IgG2 (Table 4). Hybridomas LD7 and CA6 were deposited with ATCC (10801 University Boulevard, Manassas, Va. 20110) as Deposit Numbers PTA-124631 and PTA-124632, respectively, on Nov. 21, 2017.

The vaccines induced good serum titers to their respective immunogens. Both mycolic acid binding MABs and MTB surface binding MABs were induced by whole killed MTB. MABs to one or more immunity enhancing antigens are believed to useful for preventing and/or treating MTB or other infections. TB Pep02 induced serum titers to influenza and influenza peptide (SEQ ID NO 5) and MABs were produced to the influenza peptide sequence (Table 4).

TABLE 4

Isolated and Purified Monoclonal Antibodies

| Vaccine | Mouse | MAB | Isotype | Binding |
|---|---|---|---|---|
| CRM-TB Pep01 | 1435 | LD7 I BB2 | IgG2a | TB Pep01 |
| CRM-TB Pep01 | 1435 | CA6 II GA8 | IgG2b | TB Pep01 |
| EtOH Killed MTB Lot 3 | 1323 | JG7 III D3 | IgG1 | MTB Surface |
| EtOH killed MTB Lot 4 | 1420 | AB9 I A5 | IgG1 | MTB Surface |
|  |  | GG9 II F2 | IgG1 | Mycolic Acid - MTB Surface |
|  |  | GG9 II F4 | IgG1 | Mycolic Acid - Free |
|  |  | GG9 II G2 | IgG1 | Mycolic Acid - MTB Surface |
| CRM-TB Pep02 | 1438 | FE11 II A5 | IgG1 | Influenza Peptide (Seq 5) |
| CRM-TB Pep02 | 1438 | FE11 II B3 | IgG1 | Influenza Peptide (Seq 5) |

Example 6

Phagocytic cells (HL60) differentiated according to standard protocol were incubated with ethanol killed MTB according to standard protocol. MTB were rapidly taken into the cells, but remained unchanged. In addition, the phagocytic cells did not react. In marked contrast, the addition of a MAB (purified AB9IA5) that binds to the surface of MTB caused a rapid and profound response in the phagocyte. Hybridoma cell lines that express MABs AB9 (designated in the examples as subclone IA5), GG9 (designated in the examples as subclone IIG2), and JG7 (designated in the examples as subclone IIID3) were deposited with the ATCC (Manassas, Va.) on Aug. 15, 2017. Hybridoma AB9 was assigned Accession No. PTA-124418, hybridoma GG9 was assigned Accession No. PTA-124417, and hybridoma JG7 was assigned Accession No. PTA-124416. The MTB was engulfed in vacuoles and the organism morphology was rapidly destroyed. A fluorescent-based microscopy assay was developed to examine functional antibody activity against inactivated *Mycobacterium tuberculosis* (MTB) using differentiated HL60 cells in the presence and/or absence of human complement. Bacteria: Inactivated *Mycobacterium tuberculosis* was obtained from Battelle (West Jefferson, Ohio). Stock MTB: 1 mL bacterial suspensions fixed in EtOH or glutaraldehyde at a concentration between 1 and $10\times10^8$ CFU/ml (OD600 nM=1.000). Fixative removal: Ethanol and glutaraldehyde fixatives in MTB were removed prior to staining and/or mixing with differentiated HL60 cells to prevent damage to macrophages. Centrifugation: Fixative removal, staining, destaining and washing steps were done using centrifugation at 12000 rpm for 5 min, unless noted otherwise. The location of the bacterial pellet was noted post centrifugation. Using a pipette, ~1,000 ul of supernatant from the tube was removed without disrupting the pellet. The MTB pellet was resuspended with a maximum volume of 1.2 mL per reagent and gently mixed by pipetting up and down 4-5 times.

Procedure for Auramine O Staining of MTB

One ml of stock MTB was pelleted by centrifugation, washed 3 times with sterile tissue culture grade water to remove fixative. The MTB pellet was resuspended with 1 mL of TB Auramine O and stained for 15 minutes at room temperature and then washed once with demineralized water using centrifugation. The MTB pellet was resuspended with 1 mL TB Decolorizer (Truant-Moore) for 2-3 minutes then washed once with demineralized water, again using centrifugation. The MTB pellet was resuspended with 1 mL TB Potassium Permanganate for 2-4 minutes and washed three times with demineralized water using centrifugation. The MTB pellet was resuspended in 1 mL sterile TC water. Growth and Differentiation of HL60 cells: Cells from the HL60 cell line (promyelocytic human leukemia cells: Ass#98070106, Lot 11D009; Sigma) were conditioned before use. Stock HL60s: A frozen stock vial was thawed and expanded into a T-25 flask to a density of $5\times10^5$ cells/mL in RPMI-1640 media containing 1% L-Glutamine supplemented with 10% Fetal Bovine Serum (FBS). No antibiotics were added into the culture media. Undifferentiated HL60s were conditioned for microscopy studies as follows: Cells were grown in 200 mL suspensions at 37° C. in a 5% $CO_2$ humidified atmosphere. The cells were passaged every 3-4 days at $1\text{-}1.5\times10^5$ cells/mL in RPMI-1640 media containing 1% L-Glutamine and 10% FBS with no antibiotics. Differentiated HL60s: Cells were differentiated once a week at $2\times10^5$ cells/mL in RPMI-1640 media containing 1% L-Glutamine, 20% FBS, 1.25% Dimethyl Sulfoxide (DMSO) with no antibiotics. These cells were ready for use in the assay at day 5 or 6 post induction with DMSO. Aseptically, one mL of differentiated HL60 cells at day 5 or 6 was aliquoted into a microcentrifuge tube for use in the fluorescent-based microscopy assay. ActinRed 555 Staining of Differentiated H160 cells: Differentiated HL60 cells were stained with ActinRed 555 Ready Probes reagent (Cat# R37112, Life Technologies). Two drops of ActinRed 555 dye were added per mL of media/cells which were then gently vortexed and incubated for 5-15 minutes. Antibody Test Samples: Neat serum or purified MAB samples were stored at minus 20° C. before use, thawed and diluted in Phosphate Buffered Saline, pH 7.4 (Cat#100049, Life Technologies). The test samples selected had antibodies against MTB with titers and/or binding activity confirmed by enzyme-linked immunosorbent assay (ELISA). Serum Dilution: Neat serum was diluted to a 1:100 test sample by adding 990 μL of PBS into a microcentrifuge tube followed with 10 uL of neat serum into the 990 μL PBS. All was vortexed gently to mix. Purified MAB Dilution: One mL of MAB sample was prepared by diluting the stock MAB to 100 μg/mL in PBS. The 100 μg/mL sample was further diluted to a 10 μg/mL by adding 45 μL of PBS into a microcentrifuge tube and adding 10 μL of purified MAB into the 90 μL PBS, again vortexing gently to mix. Complement: Human Complement was obtained from Thermofisher Scientific, Cat NC988107; Lot 908634 and was aliquoted and stored at minus 80° C. until use. Stored sample was diluted in cold DMEM F-12 media (Cat# D8062, Sigma) supplemented with Hepes Buffer (Cat# H0887, Sigma). Complement was diluted into a 1:16 sample by thawing in an ice bath followed by the addition of 150 μL of cold media into a microcentrifuge tube with 10 μL of human complement placed into the 150 μL of cold media which was repeatedly pipetted to mix and kept in the ice bath until use. With a Nikon Eclipse E600 Fluorescent Microscope, various combinations of test samples were examined that included: (1) ActinRed stained differentiated cells, (2) Auramine O stained MTB, (3) anti-MTB antibodies and (4) Human Complement. Individual or combinations of samples were placed in labeled tubes as with the rations (see Table 5): 100 μL HL60s: 100 μL MAB/Serum: 10 μL MTB: 10 μL C'. With a pipette, 20 μL of sample were deposited into the middle of a micro slide and examined using 100× magnification with emersion oil. The Nikon Eclipse E600 Fluorescent Microscope Camera used a professional image acquisition software to process and manages images.

TABLE 5

FluMic 001 & 002

| Slide/Tube Number | Test Sample | Time point |
|---|---|---|
| TS01 | HL60s only + ActinRed 555 | 0 min |
| TS02 | Inactivated MTB + Auramine O Stain | 0 min |
| TS03 | Differentiated HL60s + Inactivated MTB | 3-60 min |
| TS04 | Differentiated HL60s + Inactivated MTB anti-MTB/MAB AB9IA5 | 3-60 min |
| TS01 | Differentiated HL60s only + ActinRed 555 | 0 min |
| TS02 | Inactivated MTB + Auramine O Stain | 0 min |
| TS03 | Differentiated HL60s + Inactivated MTB | 3-60 min |
| TS04 | Differentiated HL60s + Inactivated MTB + anti-MTB MAB GG9IIF2 | 3-60 min |

Example 7: Antibody Stimulated Enhanced Phagocytic Activity

Studies were performed using HL 60 phagocytic cells to evaluate the ability of antibodies to specific MTB target molecules to enhance phagocytic activity against MTB. Parallel studies using Group B Streptococci (GBS) demonstrated that antibodies directed against GBS capsule could facilitate rapid phagocytosis and killing of GBS by HL 60 cells. Ethanol killed MTB was incubated in the absence of antibody with the same conditioned HL 60 phagocytic cells. While the MTB was taken inside the phagocyte, the Bacillus remained normal in size and morphology and the HL 60 cells were not stimulated and did not change appearance. The MTB bacilli and HL 60 cells were both unchanged despite having the MTB in the cell cytoplasm. This has been considered to be a problem for TB latency that MTB can persist unharmed inside phagocytic cells.

To analyze the ability of antibodies to specific MTB substances to stimulate phagocytes and enhance phagocytic activity, cloned and purified mouse monoclonal antibodies (MAB) were used to various MTB targets and epitopes (Table 4). Incubating MAB AB9 IA5 (Table 4) with MTB alone did appear to alter the shape or morphology of the bacillus. The halo zone around the bacillus (cell wall/surface matrix) was unchanged. When HL 60 phagocytic cells were added to MTB and the MAB the cells were rapidly stimulated to engulf and phagocytize the bacilli, which appeared in vacuoles not in the cytoplasm. Over 3-10 minutes the vacuoles enlarged and bacillus morphology deteriorated. These changes continued to progress over time with large blebs and protrusions appearing throughout the cell. The MTB antibody enhanced phagocytosis and the bacillus up take and destruction visualized are consistent with the phagocytosis and killing data demonstrated with antibody and GBS. The MAB AB9IA5 is an IgG1 antibody that binds to an unidentified MTB surface antigen as determined by ELISA.

To further determine the ability of antibodies to stimulate phagocytes to engulf and destroy MTB, a different purified MAB GG9 II G2 (Table 4) was utilized that binds to a mycolic acid surface epitope as measured by ELISA binding to both MTB bacilli and the mycolic acid moiety. Surprisingly when this MAB was incubated with MTB alone, the morphology changed and the bacillus enlarged, with the cell wall/surface matrix halo increasing in size. When HL 60 phagocytic cells were incubated with the MTB and the MAB the phagocytes were markedly stimulated and extended pseudopods that bound and engulfed the MTB. The pseudopods were actively moving to bring the bacilli into vacuoles and over 5-15 minutes the MTB was deformed and degraded. This anti-mycolic acid antibody promoted active phagocytic engagement of MTB and stimulated profound up-take of MTB and vacuole formation. Over the next several minutes the bacilli were degraded and destroyed. Mycolic acid is a major component of the surface matrix of MTB and considered to enable the MTB to be able to avoid effective phagocytosis and killing. Not all mycolic acid antibodies bind to the MTB bacillus (Table 4) and therefore will not stimulate phagocytes to engulf and kill MTB. This method of producing MABs that detect binding to whole MTB and target molecules and then analyzing the ability of the MAB to stimulate phagocytic HL 60 cells using fluorescent-based microscopy is useful for detecting MABs for preventing or treating TB. In addition, this method is useful for validating vaccine targets designed to induce antibodies to MTB. Example 8

Figure 7:
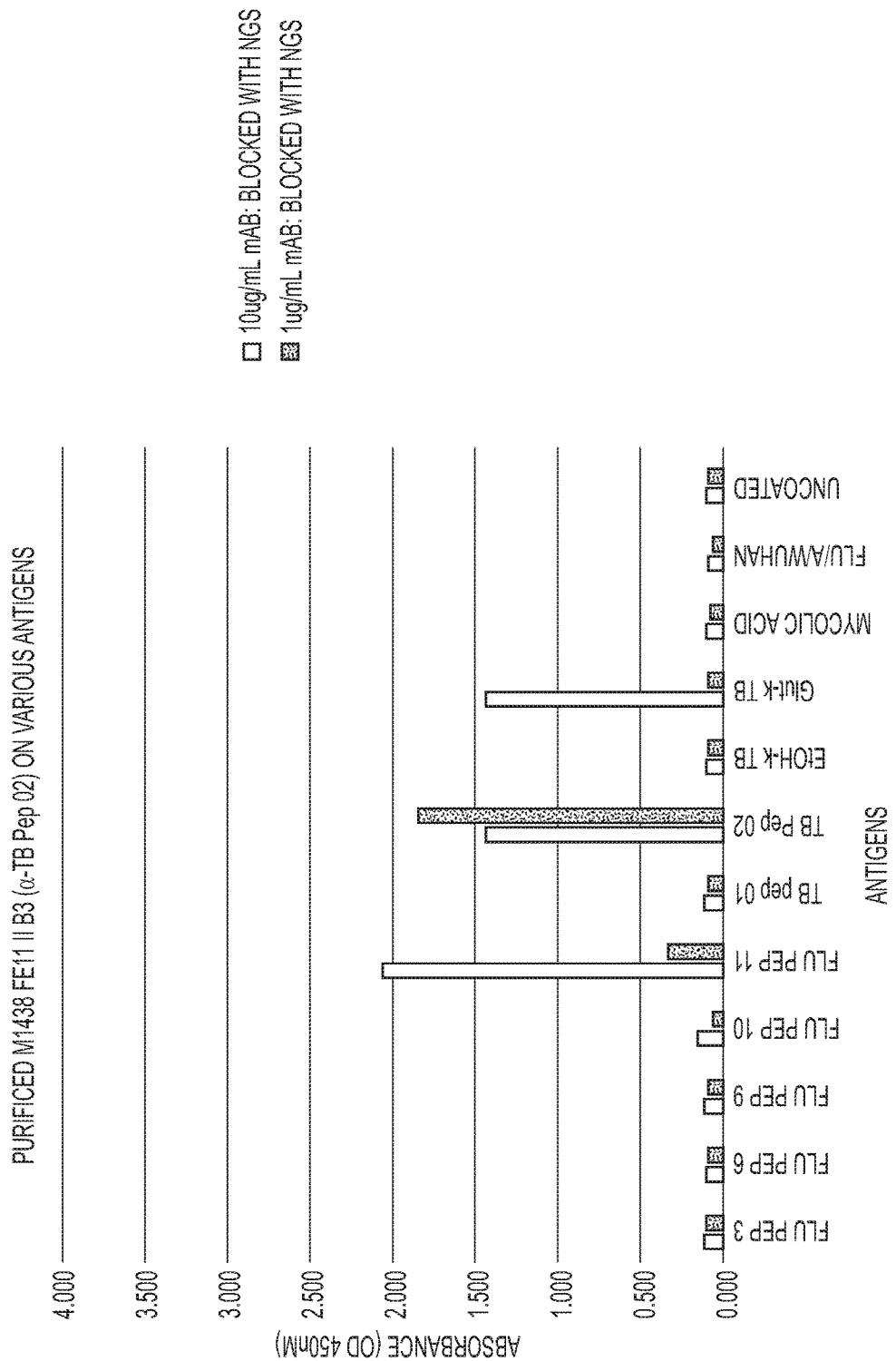
Figure 9:
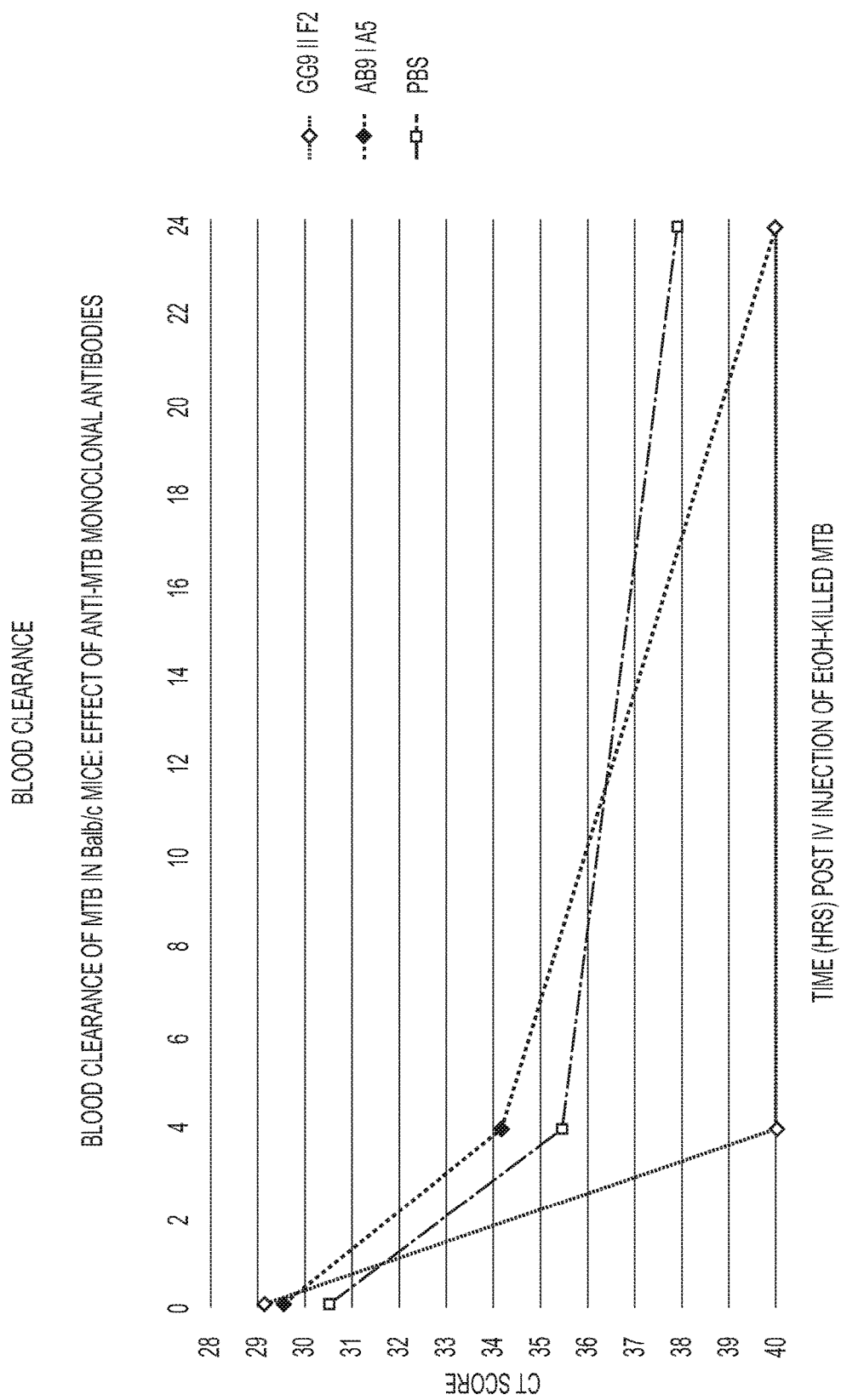
Figure 10:
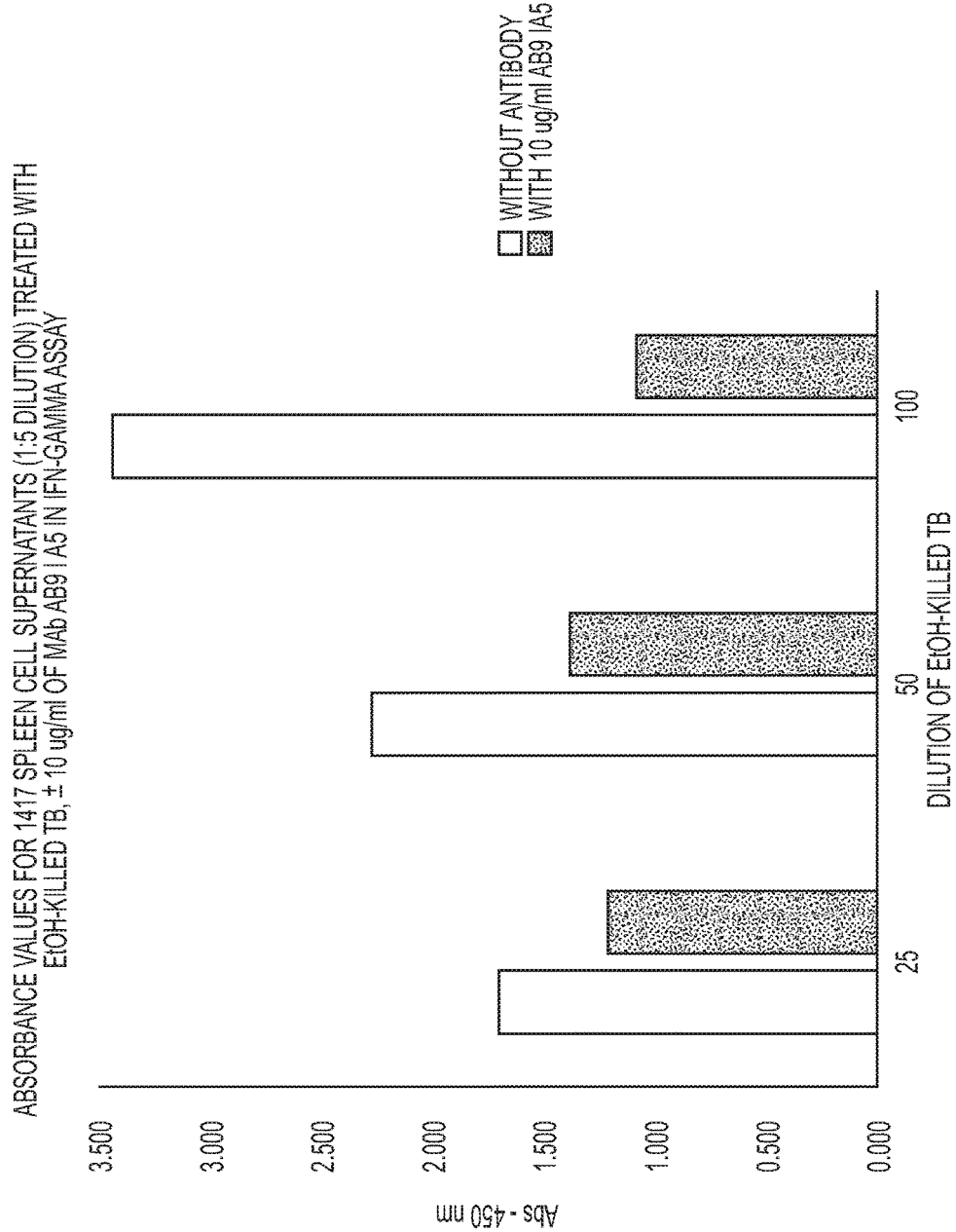
Figure 11:
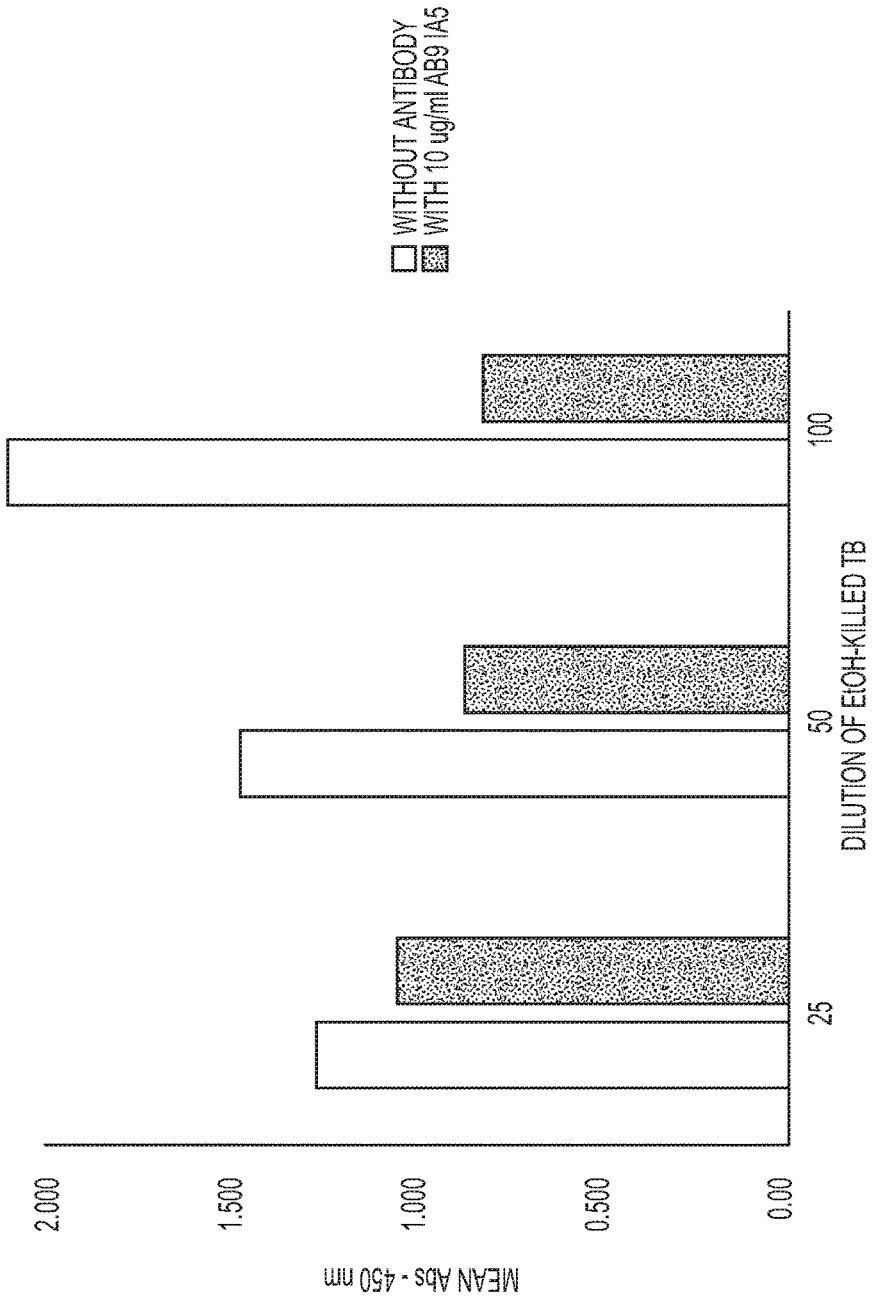
Figure 12:
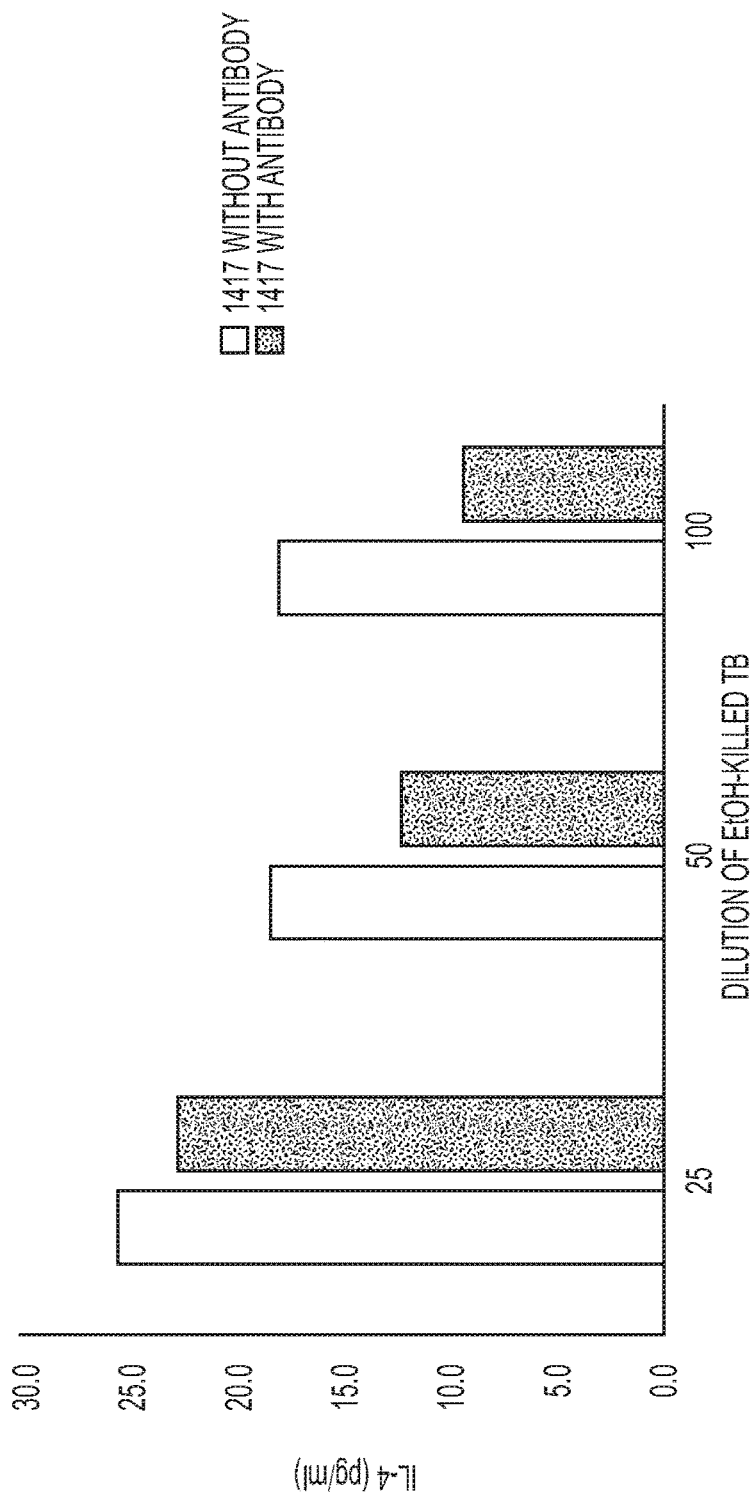

Purified MAB M1438 FE11 II B3 was induced in a mouse by immunization with non-natural, synthetically produced, MTB and Influenza (Flu) combined peptide antigen (SEQ ID NO 7) that was conjugated to the CRM protein. This combined peptide sequence contains 5 Flu peptides and one MTB peptide. Peptide 3 and Peptide 6 are non-natural Flu peptide composite epitopes of HA that combine the sequences of different Flu serotypes (SEQ ID NOs 2 and 4). Pep 9 is a combined peptide of 3 and 6. Flu Pep 10 is a NA peptide that when synthesized with Pep 3 and 6 is sequence Pep 11 (SEQ ID NOs 5 and 6). TB Pep 02 is a combination of TB Pep 01 (SEQ ID NO 1) and Flu Pep 2, 3 and 4 (SEQ ID NO 7). The MAB binding to various epitopes and antigens was analyzed by ELISA according to protocol (FIG. 7). The MAB bound well to TB Pep 02 at both 1 and 10 µg/ml and at 10 µg/ml to Flu Pep 11 and surprisingly to gluteraldehyde killed MTB (Glut-K TB). Binding to Glut-K TB, but not to ethanol killed TB (EtOH-K TB) demonstrates that each type of microbial inactivation changes the normal antigens of the organism differently producing a variety of non-natural antigens or epitopes and in this case ethanol and gluteraldehyde each alter the surface moieties of MTB differently thereby creating new and non-natural structures that are recognized by the immune system.

Example 9

Monoclonal Antibodies to MTB Enhance Mycobacterial Phagocytosis and Killing Opsonophagocytic Assay with Complement:

To assess the ability of anti-MTB MABs to enhance phagocytosis and killing of mycobacteria an opsonophagocytic killing assay was performed. HL60 cells were passed every 3-4 days at $1\times10^5$ cells/ml in a T-225 flask with 400 µl of culture media. Cells were differentiated prior to the assay at $2\times10^5$ in T-225 flask with 400 µl of differentiation media containing 1.25% DMSO. Assays were conducted in 96-well plates using HL60 cells in the presence of C1q. Briefly, 40 µl of antibody/serum, with appropriate controls, followed by 40 µl of cells at $5\times10^7$ cells/ml were added to each well with selected wells receiving 10 µl of C1q as complement. M. smegmatis was cultured overnight and percent transmission was read using a Spectronic 20D+. The bacteria were initially diluted to 50% T in 7H9 broth and diluted again with 7H9 broth to 1:500. 10 µl of the final bacterial dilution were added to each well of the 96-well plates. Plates were incubated at 36-38° C. on a shaker. After 4 hours of incubation, 10 µl from each well were transferred to a second 96-well plate containing 190 µl of a 0.1% BSA solution and thoroughly mixed. Next 100 µl from each well was transferred to a blood agar plate and incubated inverted overnight at 36-38° C. After incubation, colony which developed were counted using an AccuCount 1000 colony counter and the results recorded.

In the presence of C1q (complement) and MABs that bound to MTB" . . . HL60 cellsHL60 cells phagocytized and killed MS (50-58%) compared to control (0%). Further studies injecting ethanol killed MTB in mice showed that MTB MABs enhanced clearance of MTB from the blood of mice compared to PBS one MAB CC9 II F2 cleared MTB from the blood in 4 hrs. Another MTB MAB cleared in MTB from the blood in 24 hrs. At 24 hrs, mice given PBS control did not clear the MTB (see FIGS. 8 and 9).

Example 10

Opsonophagocytic Assay without Complement:

To assess the ability of anti-MTB MABs to enhance phagocytosis and killing of mycobacteria an opsonophagocytic killing assay was performed. U-937 cell line was conditioned for 3-4 days in media containing PMA. For PMA treatment, U-937 cells were seeded into six flasks at $2.5\times10^5$ cells/ml or wells of a 96-well plate at $2\times10^6$ cells/well, either in 200 μl of differentiation media containing 0.005% PMA. 24 hours post-differentiation, PMA-containing media was replaced with cell culture media. Assays were conducted in 96-well plates using U-937 cells without complement. Briefly, 40 μl of antibody/serum, with appropriate controls, followed by 40 μl of cells at $5\times10^7$ cells/ml were added to each well with selected wells receiving 10 μl of C1q as complement. *M. smegmatis* was cultured overnight and percent transmission was read using a Spectronic 20D+. The bacteria were initially diluted to 50% T in 7H9 broth and diluted again with 7H9 broth to 1:500. 10 μl of the final bacterial dilution were added to each well of the 96-well plates. Plates were incubated at 36-38° C. on a shaker. After 4 hours of incubation, 10 μl from each well were transferred to a second 96-well plate containing 190 μl of a 0.1% BSA solution and thoroughly mixed. Next 100 μl from each well was transferred to a blood agar plate and incubated inverted overnight at 36-38° C. After incubation, colonies which developed were counted using an AccuCount 1000 colony counter and the results recorded.

The analysis of the ability of MABs to MTB to enhance phagocytosis and killing of mycobacteria in macrophages was conducted with conditioned U937 cells incubated with MS and monoclonal antibodies to MTB. Without antibody MS was not killed, however, in marked contrast, U937 with G6911G2 demonstrated enhanced killing at 67% (OP064 2015).

Example 11

Anti-TB MABs modulate IL4 and IFNγ cytokine induction in the presence of MTB. Spleen cells from mice previously injected with ethanol killed MTB were incubated with ethanol killed MTB to induce cytokines. Monoclonal antibodies to MTB were pre-incubated with the ethanol killed MTB to determine if MABs could modulate cytokine production by pre-sensitized spleen cells. Mouse spleen cells from mice previously injected with ethanol killed MTB were incubated with MTB. There was a brisk production of both IL4 and IFNγ by spleen cells in the absence of antibody to MTB. MAB to MTB was able to modulate both IL4 and IFNγ production (see, FIGS. 10-13) and decrease the cytokine responses for Th1 and Th2 immunity.

Example 12

MABs that Modulate Immunity

A first step for anti-microbial opsonic MABs is binding to the organism that is to be treated. Opsonic MABs disclosed herein are useful for prevention or treatment of MTB infections. To be maximally therapeutic, MABs have the capability to bind to susceptible, multidrug resistant (MDR) MTB and extremely drug resistant (XDR) MTB. As MTB becomes more drug resistant, surface structures are altered and MABs that enhance MTB opsonization and phagocytic killing bind drug sensitive and highly resistant strains and are the most useful.

Preparation of bacteria for live binding assay: PBS/BSA solution was prepared by diluting 670 μl of 30% BSA (Sigma-Aldrich life science, Chemie GmBH) in 200 ml of PBS (pH 7.2-7.4). PBS-T/BSA solution was prepared by diluting 670 μl of 30% BSA in 200 ml PBS-T (pH 7.4). Susceptible *M. tuberculosis* strains were diluted after OD measurement, by adding 1 ml of the bacteria in 14 ml PBS/BSA, centrifuging the resulting mixture for 10 minutes at room temperature (2600 rpm) using a Heraeus multifuge (Thermo Fisher Scientific, Waltham, Mass.) and discarding the supernatant. The pellet was re-suspended in 4 ml PBS/BSA, re-centrifuged and the supernatant was discarded. A final re-suspension was made in 1.5 ml PBS/BSA solution and the bacteria were serially diluted.

Addition of purified MABs and detection antibody to bacteria: The MABs were diluted from stock concentrations (according to the plate map) in calculated volumes of PBS-T and 60 μl of each resulting dilution was dispensed in each well of a round-bottom dilution plate (Sigma-Aldrich life science, Chemie GmBH) according to the designed plate map. Fifty microliters (50 μl) of the diluted MABs were taken from the first dilution plate and introduced into the wells containing the bacteria. The wells without MAB had an equivalent volume of PBS/BSA solution. The plates were sealed and incubated for 1 hr at 37° C. in a shaking incubator (Thermostar, BMG Labtech, Ortenberg, Germany) (250 rpm). After incubation, the plates were centrifuged at 25° C. for 5-10 minutes (2600 rpm). The entire solution (150 μl) was pipetted out and 200 μl of PBST/BSA solution was dispensed into all the wells and re-centrifuged. This step was repeated once and the solution was pipetted out completely. A 100 μl volume of diluted goat anti-mouse IgG1 detection antibody was dispensed into each well of the plate, sealed and incubated in a shaking incubator at 37° C. for 30 minutes (250 rpm). The plate was re-centrifuged for 10 minutes at 25° C. (2600 rpm) and washed three times with 200 μl PBS-T/BSA.

After the final wash, the solution was pipetted out completely, 100 μl of TMB substrate solution was dispensed into the wells and mixed thoroughly by pipetting the solutions up and down. The plate was incubated in the dark for 15 minutes at room temperature without sealing. One hundred microliters (100 μl) of TMB stop solution was added into the wells after the incubation and centrifuged for 5 minutes at 25° C. (2600 rpm). A 180 μl volume of the supernatant was carefully taken out (without the pellet) per well, and transferred onto corresponding wells of the ELISA NUNC Maxisorp flat-bottom plate. The NUNC plate was read immediately at either 450 nm or 630 nm, depending on the TMB STOP solution used.

Both GG9 and JG7 bound to live and alcohol fixed MTB including susceptible, MDR and XDR strains (Elisa OD>1.0 @ 450 nm). At 10 μg/ml both MABs bound to XDR strains at OD 3.0, while binding activity at lower concentrations showed that MAB binding was different between the XDR strains and JG7 or GG9. Combinations of different MABs might be useful to treat MTB especially MDR and XDR strains.

Example 13

The 16 KD heat shock protein (HSP) is important for MTB to persist in cell sand tissues in a latent state. Studies have shown that IgA MABs can provide passive protection against MTB in mice and that IgA not IgG is important for this activity. (Lopez et al., J Med Micro 299:447, 2009) IgG MABs have been developed to the 16KD HSP using CRM-peptide vaccine. Both active and passive IgG provide an effective method for treating or preventing MTB latency.

Other embodiments and uses of the invention will be apparent to those skilled in the art from consideration of the specification and practice of the invention disclosed herein. All references cited herein, including all publications and U.S. and foreign patents and patent applications, are specifically and entirely incorporated by reference including U.S. Patent Application Publication No. 2014/20150064198 entitled “Enhancing Immunity to Tuberculosis” filed Aug. 29, 2014, U.S. Patent Application Publication No. 2013/0195909 entitled “Composite Antigenic Sequences and Vaccines” filed Jan. 25, 2013, U.S. Patent Application Publication No. 2011/0281754 entitled “Compositions and Method for Detecting, Identifying and Quantitating Mycobacterial-Specific Nucleic Acid” filed Apr. 26, 2011, U.S. Patent Application Publication No. 2009/0081202 entitled “Immunogenic Compositions and Methods” filed Aug. 27, 2008, and U.S. Provisional Application No. 61/746,962 entitled “Multipurpose Compositions for Collecting, Transporting and Storing Biological Samples” filed Dec. 28, 2012. The term comprising, where ever used, is intended to include the terms consisting and consisting essentially of. Furthermore, the terms comprising, including, containing and the like are not intended to be limiting. It is intended that the specification and examples be considered exemplary only with the true scope and spirit of the invention indicated by the following claims.

The invention claimed is:

1. A method for treating infection of drug-resistant *Mycobacterium tuberculosis* (MTB) in a mammal comprising:
    providing an immunological composition containing an antibody that binds to an epitope of an antigen of MTB, wherein the antigen is obtained or derived from MTB that has been killed by exposure to a chemical and/or physical treatment wherein, the epitope is not immunologically available prior to the chemical and/or physical treatment, the antigen comprises peptidoglycan, mycolic acid, an MTB heat-shock protein, or lipoarabinomannan, and the chemical and/or physical treatment comprises exposure to about 70% ethanol or about 2% glutaraldehyde, activated with sodium biocarbonate; and administering the composition to the mammal, wherein the composition induces the immunological system of the mammal to promote phagocytosis and killing MTB infected cells.

2. The method of claim 1, wherein the phagocytosis and killing is enhanced in the presence of the composition as compared to the phagocytosis and killing of mycobacteria in the absence of the composition.

3. The method of claim 1, wherein the composition comprises polyclonal antibodies, monoclonal antibodies, or both polyclonal and monoclonal antibodies.

4. The method of claim 2, wherein the epitope is chemically or physically altered as compared with the naturally occurring epitope.

5. The method of claim 1, wherein the immunological composition is an adjunctive therapy in combination with administration of an antibiotic.

6. The method of claim 1, wherein administration of the immunological composition clears MTB from the blood of the mammal.

7. The method of claim 1, wherein the immunological composition modulates immunity to drug-resistant MTB.

8. The method of claim 1, wherein the immunological composition is administered at a therapeutically-effective dose.

9. A method of treating an infection in a mammal caused by a *Mycobacterium tuberculosis* (MTB) microorganism comprising:

administering a composition to the mammal, wherein the composition contains an antibody that binds to an epitope of an MTB antigen, wherein:

the epitope is immunologically exposed only after the MTB microorganism is exposed to a chemical and/or physical treatment sufficient to kill the microorganism;

the MTB antigen comprises peptidoglycan, mycolic acid, an MTB heat-shock protein or lipoarabinomannan; and the chemical and/or physical treatment comprises exposure of the MTB microorganism to about 70% ethanol or about 2% glutaraldehyde, activated with sodium bicarbonate, in a manner sufficient to kill the MTB microorganism;

inducing the immunological system of the mammal to promote opsonophagocytosis of cells infected with the MTB microorganism.

10. A method of treating an infection caused by a *Mycobacterium tuberculosis* (MTB) microorganism comprising:

exposing MTB microorganisms to a chemical and/or physical treatment which would be sufficient to kill MTB microorganisms, wherein the chemical and/or physical treatment comprises exposure to about 70% ethanol or about 2% glutaraldehyde, activated with sodium bicarbonate, that immunologically exposes an MTB epitope that is not immunologically exposed with untreated MTB microorganisms;

generating antibodies to the exposed MTB epitope; and administering the antibodies generated to a mammal with an active or suspected MTB infection, wherein administration induces a humoral immunological response that promotes opsonophagocytosis of cells infected with MTB microorganisms.

11. The method of claim 10, wherein the chemical and/or physical treatment further comprises additional exposure to heat, alcohol, glutaraldehyde and/or sonication.

12. The method of claim 10, wherein the MTB epitope is located on a peptidoglycan, a mycolic acid, a heat-shock protein, or a lipoarabinomannan glycolipid of MTB.

13. The method of claim 9, wherein administration of the immunological composition clears MTB from the blood of the mammal.

14. The method of claim 9, wherein the composition modulates immunity to drug-resistant MTB.

15. The method of claim 9, wherein the composition is administered at a therapeutically-effective dose.

16. The method of claim 10, wherein antibodies clear MTB from the blood of the mammal.

17. The method of claim 10, wherein the antibodies modulate immunity to drug-resistant MTB.

18. The method of claim 10, wherein the antibodies are administered at a therapeutically-effective dose.

* * * * *